United States Patent [19]
Sarvazyan

[11] Patent Number: 5,860,934
[45] Date of Patent: *Jan. 19, 1999

[54] METHOD AND DEVICE FOR MECHANICAL IMAGING OF BREAST

[75] Inventor: Armen Paruir Sarvazyan, East Brunswick, N.J.

[73] Assignee: Artann Corporation, Lambertville, N.J.

[*] Notice: The term of this patent shall not extend beyond the expiration date of Pat. No. 5,524,636.

[21] Appl. No.: 607,646

[22] Filed: Feb. 27, 1996

Related U.S. Application Data

[63] Continuation-in-part of Ser. No. 994,109, Dec. 21, 1992, Pat. No. 5,524,636.

[51] Int. Cl.[6] .................................................. A61B 08/12
[52] U.S. Cl. .......................... 600/587; 600/437; 600/561
[58] Field of Search ......................... 128/660.01, 660.02, 128/660.05, 660.07, 661.01, 661.02, 661.03, 774, 748; 600/561, 437, 587, 438, 441, 443, 447–449

[56] References Cited

U.S. PATENT DOCUMENTS

| | | | |
|---|---|---|---|
| 4,250,894 | 2/1981 | Frei et al. | 128/774 |
| 4,423,738 | 1/1984 | Newgard | 128/672 |
| 4,580,574 | 4/1986 | Gavish | 128/661.03 |

(List continued on next page.)

OTHER PUBLICATIONS

C.R. Gentle, *Mammobarography: A possible method of mass breast screening* (1988) J. Biomed. Eng., vol. 10, pp. 124–126.

R.M. Lerner et al., *Sono–Elasticity: Medical Elasticity Images Derived From Ultrasound Signals in Mechanically Vibrated Targets* (1988) Acoustical Imaging, vol. 16, p. 317.

T.A. Krouskop et al., *A Pulsed Doppler Ultrasonic System for Making Non–Invasive Measurement of Mechanical Properties of Soft Tissue* (1987) 24 J. Rehab. Res. Dev., vol. 24, p. 1.

(List continued on next page.)

*Primary Examiner*—Robert L. Nasser
*Attorney, Agent, or Firm*—Mathews, Collins, Shepherd & Goudl

[57] ABSTRACT

A method and devices in accordance with the present invention enable detecting regions of breast tissue having modulus of elasticity different from that of surrounding glandular tissue using a pressure sensing array. Detection of breast tumors is based on analyzing features of the stress pattern on the surface of an examined tissue that appear as a deviation from a stress pattern for a relatively homogeneous normal tissue. In one embodiment of the invention, a pressure sensor array, data acquisition circuit, and a microprocessor are mounted in a hand held pad. Detection of nodules is achieved by analyzing the dynamic and spatial features of the pressure pattern while the probe pressed to the breast is periodically moved transversely to the ribs. The ribs play a role as an amplifier of the measured effect. The device will be able to objectively detect the presence of lumps in a breast and provide a warning signal. Another embodiment of the invention is a clinical device for imaging the mechanical structure of the examined breast and diagnosing diseases accompanied by changes in the elasticity of breast tissue. This embodiment is made up of an electronically controlled mechanical scanning unit incorporated into a patient support bed. The mechanical scanning unit includes a compression mechanism and positioning system, a local pressure source located opposite a pressure sensor array, and electronic control and interface circuitry. The local pressure source is either a roller moving over the examined breast, or in another embodiment, an indenter which can be moved in all three dimensions and be controlled either automatically by a computer or manually by a mouse. In yet another embodiment, the mechanical scanning system serves as a biopsy guidance means and determines target lesions in the breast to be reached by a biopsy gun or an aspiration needle.

8 Claims, 19 Drawing Sheets

U.S. PATENT DOCUMENTS

| | | | |
|---|---|---|---|
| 4,799,491 | 1/1989 | Eckerle | 128/672 |
| 4,802,488 | 2/1989 | Eckerle | 128/672 |
| 4,860,761 | 8/1989 | Yamasaw et al. | 128/686 |
| 5,078,142 | 1/1992 | Siczek et al. | 128/653.1 |
| 5,099,848 | 3/1992 | Parker et al. | 128/661.07 |
| 5,107,837 | 4/1992 | Ophir et al. | 128/660.01 |
| 5,115,808 | 5/1992 | Popovic et al. | 128/660.02 |
| 5,265,612 | 11/1993 | Sarvazyan et al. | 128/660.01 |
| 5,293,870 | 3/1994 | Ophir et al. | 128/660.01 |
| 5,524,636 | 6/1996 | Sarvazyan et al. | 128/660.01 |

OTHER PUBLICATIONS

A.P. Sarvazyan et al., *Biophysical Bases of Elasticity Imaging* (1995) Acoustical Imaging, vol. 21, pp. 223–240.

P. Strax *Control of Breast Cancer Through Mass Screening* (Mar./Apr. 1989) Hospimedica, pp. 35–40.

Y. Yamakoshi et al., *Ultrasonic Imaging of Internal Vibration of Soft Tissue Under Forced Vibration* (1990), IEEE Transactions on Ultrasonics, Ferroelectric, and Frequency Control, vol. 7(2), p. 45.

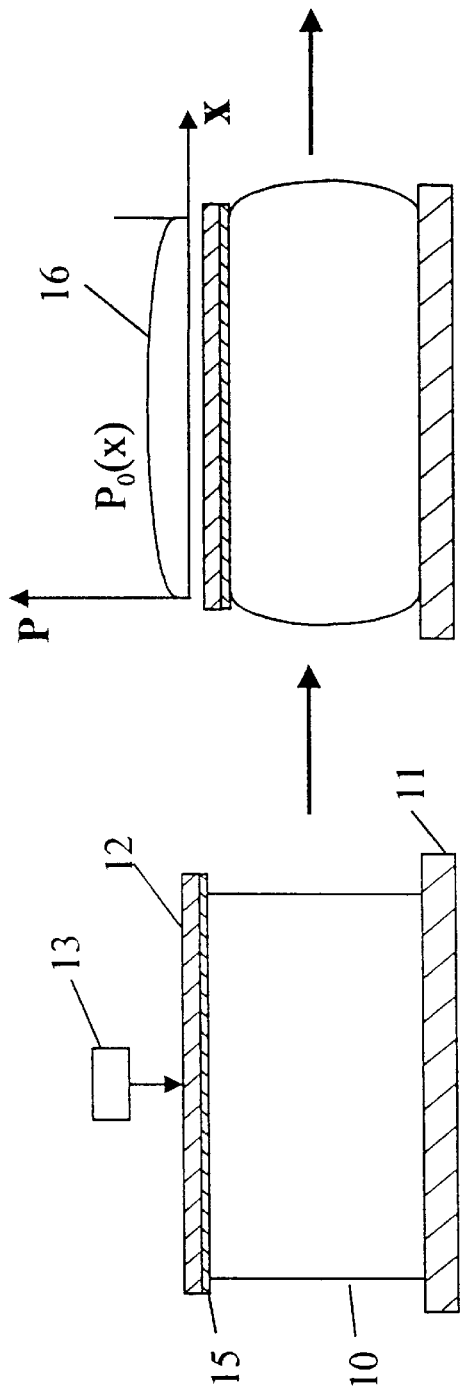
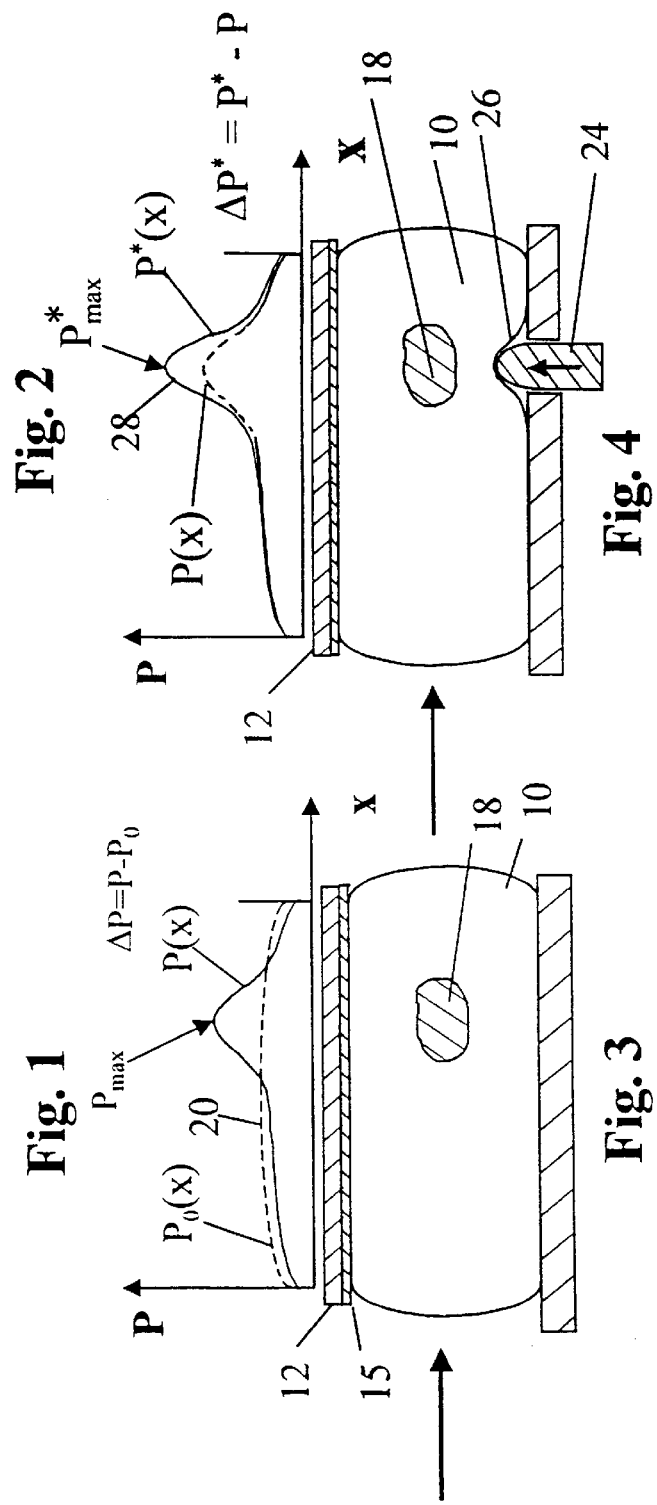
Fig. 1
Fig. 2
Fig. 3
Fig. 4

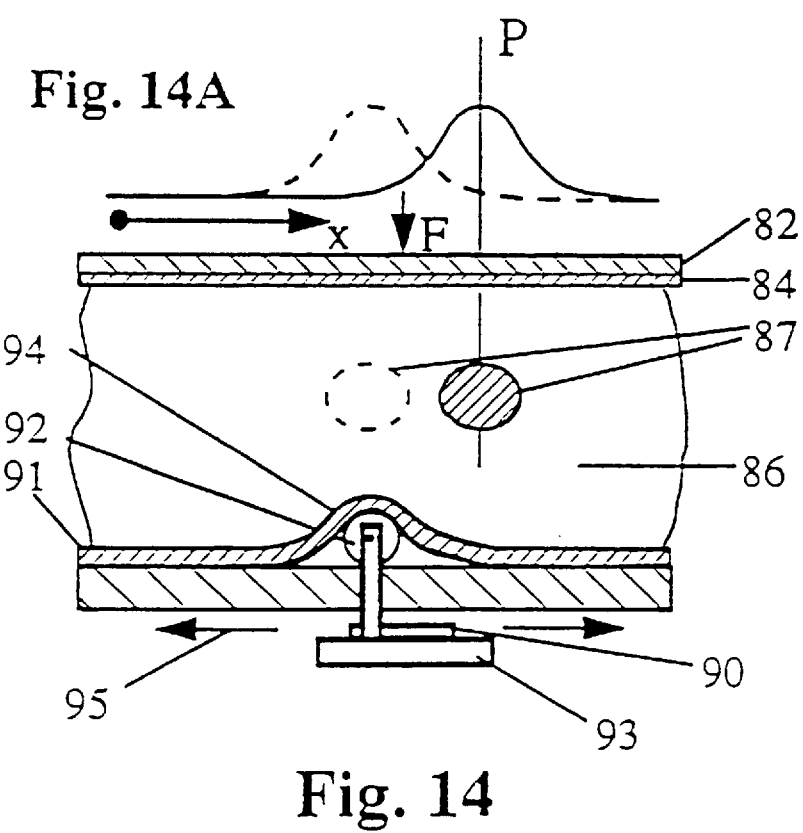

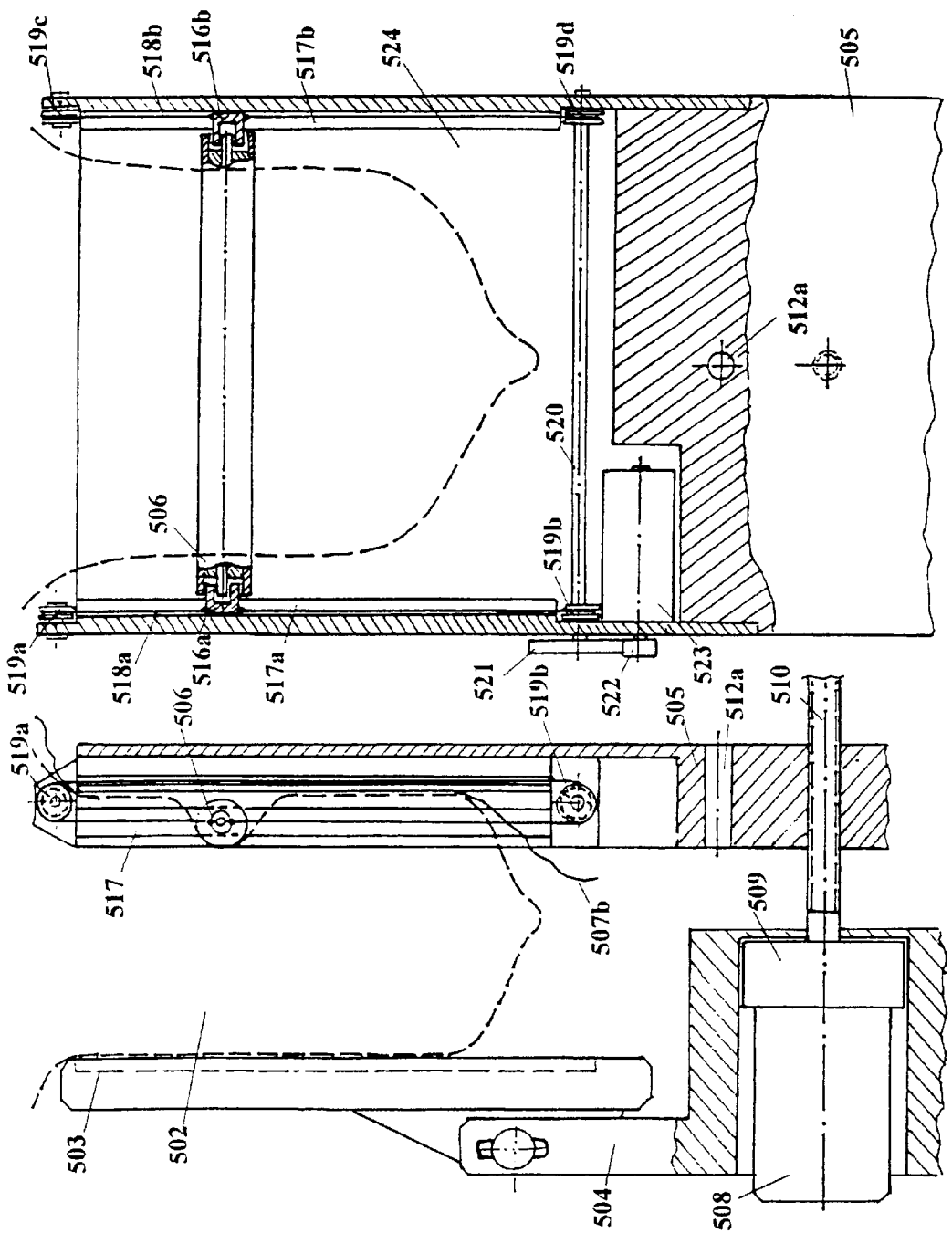

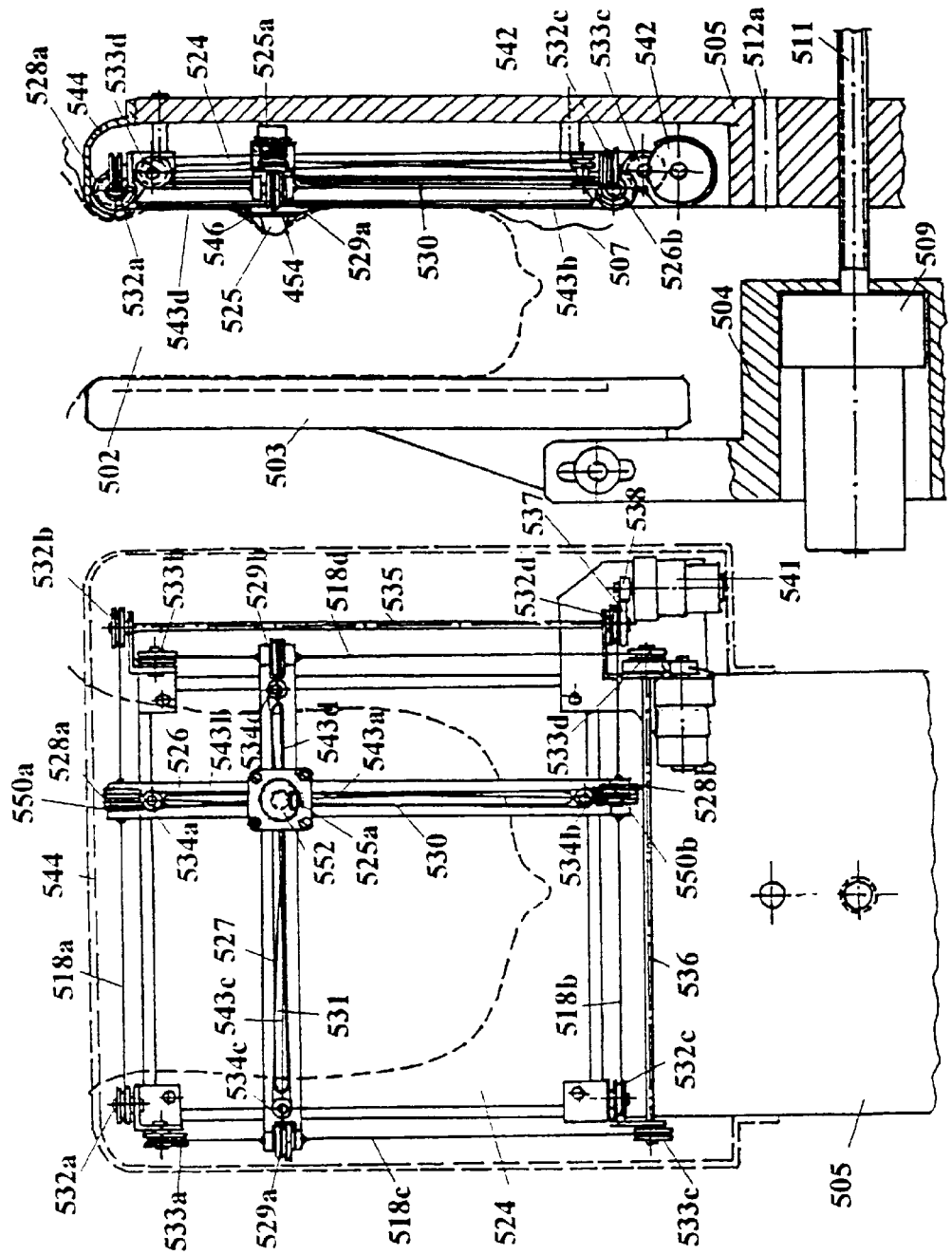

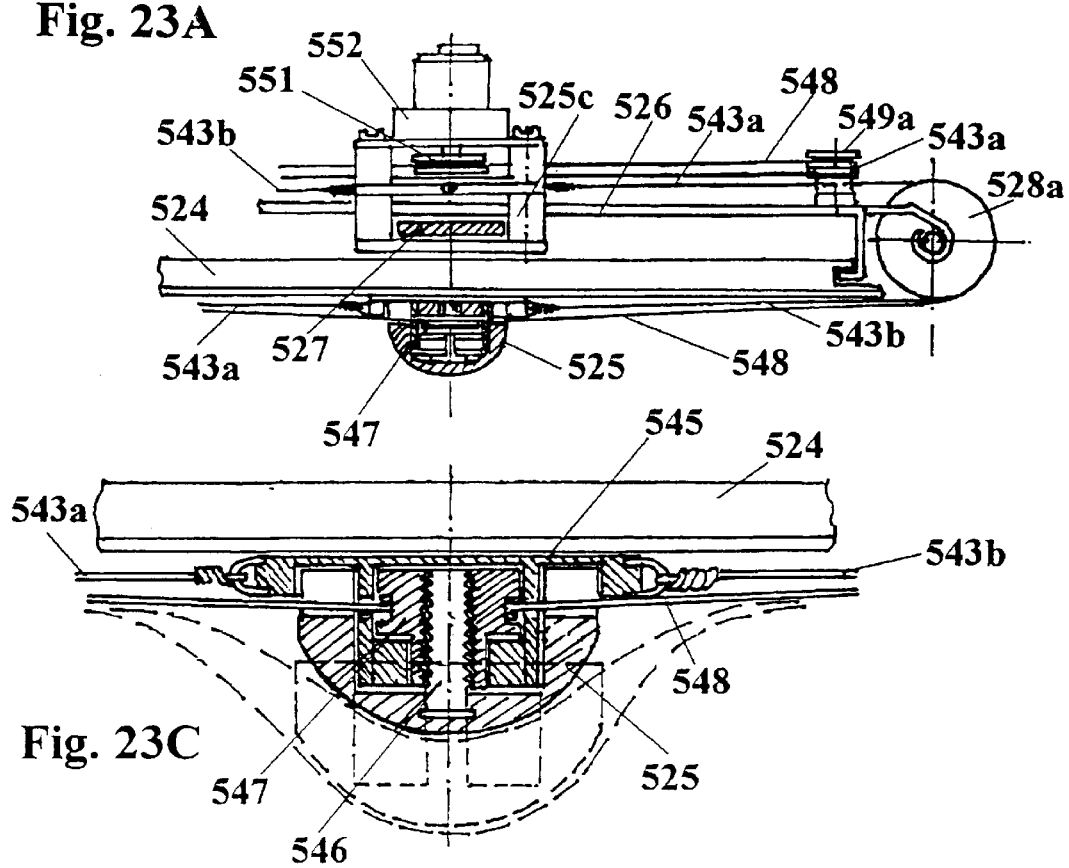
Fig. 23A
Fig. 23C
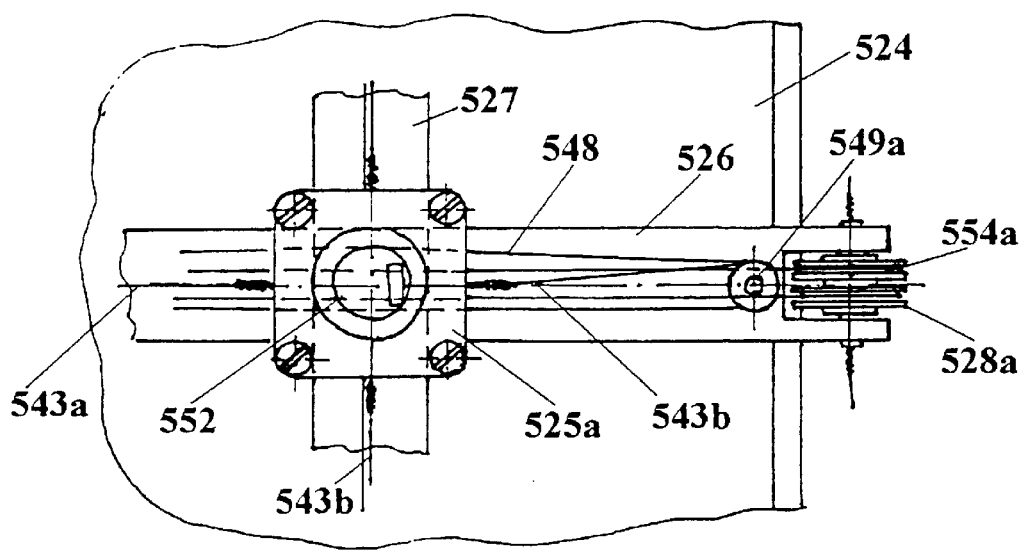
Fig. 23B

METHOD AND DEVICE FOR MECHANICAL IMAGING OF BREAST

CROSS REFERENCE TO RELATED APPLICATION

This application is a continuation-in-part of U.S. Pat. application Ser. No. 07/994,109, filed Dec. 21, 1992, now U.S. Pat. No. 5,524,636 the full disclosure of which is hereby incorporated by reference herein.

This invention was made with government support under SBIR Grant No. 1 R43 CA65246-01 A1 awarded by the National Institute of Health, National Cancer Institute. The government has certain rights in this invention.

BACKGROUND OF THE INVENTION

1. Technical Field

The present invention relates to a method and apparatus for detecting regions in the tissue with the elasticity different from that of the surrounding tissues using a pressure sensing array for diagnosing breast cancer and other breast diseases accompanied by changes in the tissue elasticity.

2. Description of the Prior Art

Diagnosing early formation of tumors, particularly those caused by cancer, has been a problem that has been attempted to be solved using various techniques, such as ultrasonic imaging, nuclear magnetic resonance imaging, x-rays, and the like. Each of these techniques have limitations, including the application of radiation to the body, which may be harmful to the body being tested.

One of the safest and oldest techniques of detecting diseased tissue is palpation. Palpation, that is, examination using the sense of touch, is based on the significant differences in elasticity of normal tissues and certain lesions. Palpation has been a commonly used technique for detecting prostate and breast cancer. Surprisingly, over 90% of breast cancer is first detected by women themselves (Strax P., *Control of breast cancer through mass screening,* Hospimedica, March/April, pp. 35–40 (1989)), in spite of palpation being very subjective, not able to detect tumors of less than about 8 mm in diameter, and, besides, being capable of sensing lumps only when their elastic modulus is a few times higher than that for normal glandular tissue. Nevertheless, the manual palpation till now is one of the major methods of clinical examination of the breast just because of the great scale changes of mechanical properties of tissues in the course of development of cancer. Many tumors that are currently considered "nonpalpable" because of their small size or insufficiently high Young's modulus, nevertheless, can be detected mechanically if a more sensitive instrument than a finger could be used. Thus, development of a method that will enable physicians to obtain quantitative objective information on changes of elasticity of breast tissues with sensitivity and spatial resolution considerably higher than that of palpation would be a significant step in the early diagnostics of breast cancer.

Various types of devices mimicking palpation to detect tumors using different types of pressure sensors have been suggested. For example, Frei et al., U.S. Pat. No. 4,250,894, have proposed an instrument for breast examination that uses a plurality of spaced piezoelectric strips which are pressed into the body being examined by a pressure member which applies a given periodic or steady stress to the tissue beneath the strips. A different principle for evaluating the pattern of pressure distribution over a compressed breast was proposed by Gentle (Gentle CR, *Mammobarography: a possible method of mass breast screening,* J. Biomed. Eng. 10, 124–126, 1988). The pressure distribution is monitored optically by using the principle of frustrated total internal reflection to generate a brightness distribution. Using this technique, referred to as "mammobarography," simulated lumps in breast prostheses have been detected down to a diameter of 6 mm. According to Gentle, this technique can be used for mass breast screening; however, no quantitative data on lumps in a real breast was ever published. The failure has been explained by the insufficient sensitivity of the registration system. It should be noted, that most of the development of pressure sensors for medical applications has been done not for mimicking palpation but for monitoring blood pressure and analyzing propagation of pulse waves in blood vessels (See, for example, U.S. Pat. Nos. 4,423,738; 4,799,491; 4,802,488; 4,860,761).

Another approach to evaluate elasticity of the tissues uses indirect means, such as conventional imaging modalities (ultrasound or MRI) which are capable to detect motion of a tissue subjected to an external force. One approach attempts to determine the relative stiffness or elasticity of tissue by applying ultrasound imaging techniques while vibrating the tissue at low frequencies. See. e.g., K. J. Parker et al, U.S. Pat. No. 5,099,848; R. M. Lerner et al., *Sono-Elasticity: Medical Elasticity Images Derived From Ultrasound Signals in Mechanically Vibrated Targets,* Acoustical Imaging, Vol. 16, 317 (1988); T. A. Krouskop et al.,*A Pulsed Doppler Ultrasonic System for Making Non-Invasive Measurement of Mechanical Properties of Soft Tissue,* 24 J. Rehab. Res. Dev. Vol. 24, 1 (1987); Y. Yamakoshi et al., *Ultrasonic Imaging of Internal Vibration of Soft Tissue Under Forced Vibration,* IEEE Transactions on Ultrasonics, Ferroelectrics, and Frequency Control, Vol. 7, No. 2, Page 45 (1990).

Another method proposed for measuring and imaging tissue elasticity is described in Ophir et al., U.S. Pat. Nos. 5,107,837, 5,293,870, 5,143,070 and 5,178,147. This method includes emitting ultrasonic waves along a path into the tissue and detecting an echo sequence resulting from the ultrasonic wave pulse. The tissue is then compressed (or alternatively decompressed from a compressed state) along the path and during such compression, a second pulse of ultrasonic waves are sent along the path into the tissue. The second echo sequence resulting from the second ultrasonic wave pulse is detected and then the differential displacement of selected echo segments of the first and second echo sequences are measured. A selected echo segment of the echo sequence, i.e., reflected RF signal, corresponds to a particular echo source within the tissue along the beam axis of the transducer. Time shifts in the echo segment are examined to measure compressibilities of the tissue regions.

Thus, since current prior art methods and devices for detecting lesions in breast by evaluating tissue elasticity are inferior to manual palpation, there still remains a need for a simple and effective device for the detection of breast cancer.

OBJECTS AND SUMMARY OF THE INVENTION

It is therefore a primary objective to provide a method and device for the detection of abnormalities of tissues accompanied by the changes in their elasticity, such as those caused by cancer, which are based on a new technology of medical imaging described in the generic patent application, referred to herein as Mechanical Imaging (MI). The essence of MI is the reconstruction of the internal structure of soft body tissues by measuring a surface stress pattern using a pressure sensing array. The pattern of mechanical stress and its changes as a function of applied pressure and time contain comprehensive information on the mechanical properties and geometry of the internal structures of the body tissues.

The applications of MI devices are those fields of medicine where palpation is proven to be a sensitive tool in detecting and monitoring diseases, including breast cancer. Despite the obvious usefulness of the diagnostic information obtained by palpation, there are no technical means and devices capable of yielding data similar to that obtained by the finger of a skilled examiner. Another object of this invention is to provide such a capability. Other objects and advantages will become apparent from the description and drawings which follow.

The method and devices in accordance with the present invention enable the user to detect regions of breast tissue having elasticity modulus different from that of surrounding glandular tissue using a pressure sensing array. Detection of breast tumors is based on analyzing features of the stress pattern on the surface of an examined tissue that appear as a deviation from a stress pattern for a relatively homogeneous normal tissue.

In one embodiment of the invention a pressure sensor array, data acquisition circuit, and a microprocessor are mounted in a hand held pad. Detection of nodules is achieved by analyzing the dynamic and spatial features of the pressure pattern while the probe pressed to the breast is periodically moved transversely to the ribs. The ribs play a role as amplifier of the measured effect. The device will be able to objectively detect the presence of small lumps in a breast (e.g., about 5 mm in diameter) and provide a warning signal.

Another embodiment of the invention is a clinical device for imaging mechanical structure of the examined breast and diagnosing diseases accompanied by changes in the elasticity of breast tissue. This embodiment comprises electronically controlled mechanical scanning unit incorporated into a patient support bed. The mechanical scanning unit includes a compression mechanism and positioning system, a local pressure source opposing a pressure sensor array, and electronic control and interface circuitry. The local pressure source is either a roller which is moved over the examined breast, or in another embodiment, an indenter which can be moved in all three dimensions.

In another embodiment, the mechanical scanning system serves as a biopsy guidance means and determines target lesions in the breast to be reached by the biopsy gun or aspiration needle.

Before referring specifically to the drawings, and without being bound by any particular posited theory, the theoretical aspects of the invention are discussed. The pressure pattern on the surface of an investigated tissue portion together with given boundary conditions enable one to reconstruct internal structures in underlying tissue and to evaluate relative hardness and softness of tissue in localized areas. The present invention expands on teachings of how elasticity differences in localized areas inside of tissue and the stress pattern on the surface of the tissue are inter-related and that this relationship forms the basis for a method of detecting and quantifying tissue abnormalities.

When calculating the mechanical properties of tissues, calculations are based on a model of the tissue as being linearly elastic and incompressible media. Such an approach is a first approximation which is sufficient to solve all questions arising in mechanical elasticity imaging.

Accordingly, the graphical representations discussed below in the detailed description of the invention are based on calculations from the general equations presented below. The following equations are general equations for three dimensional linear theory of elasticity for in-compressible media like tissues or another water based system, that is a system having a Poison's ratio of 0.5 (Sarvazyan et al., *Biophvsical Bases of Elasticity Imaging,* Acoustical Imaging, Vol. 21, 223, 1995).

These are equations of dynamic equilibrium: pressure P.

An additional equation is the equation of incompressibility showing that divergence of vector of displacement equals zero:

$$\frac{\partial U}{\partial x} + \frac{\partial V}{\partial y} + \frac{\partial W}{\partial z} = E_{xx} + E_{yy} + E_{zz} = 0$$

This last equation represents the condition that when force is applied to the soft tissue, all the deformation of tissue is related to changes of the shape of the soft tissue but not the volume, because Poison's ratio is 0.5, that is the bulk compressional modulus of soft biological tissues is many orders of magnitude higher than the shear elasticity modulus.

The mechanical characteristics of living tissue not only involve elasticity as discussed, but also viscosity. Thus, the tissue is a viscoelastic material that requires description in both viscous and elastic components. Viscosity affects the information received because with a viscoelastic tissue, there is a time delay between force application and any displacement that occurs. In a dynamic mode where force is applied in time, the development of stresses in time provides the information on viscosity.

In the case of viscoelastic media, the components of the stress tensor in equation (2) should have the following additional terms for shear viscosity, $\mu$ $$2\mu \cdot \frac{\partial E_{ij}}{\partial t}$$

The shear modulus and Young's modulus of soft tissue are different by a factor of 3, because Poison's ratio is 0.5. While either modulus can be used for examination of the tissue, Young's modulus is used in the description of the present invention.

In the case of harmonic disturbances, temporal dependence can be easily removed from these equations and the system of the differential equations for amplitudes will be obtained.

$$\frac{\partial \sigma_{xx}}{\partial x} + \frac{\partial \sigma_{xy}}{\partial y} + \frac{\partial \sigma_{xz}}{\partial z} = \rho \frac{\partial^2 U}{\partial t^2} \qquad (1)$$

$$\frac{\partial \sigma_{xy}}{\partial x} + \frac{\partial \sigma_{yy}}{\partial y} + \frac{\partial \sigma_{yz}}{\partial z} = \rho \frac{\partial^2 V}{\partial t^2}$$

$$\frac{\partial \sigma_{xz}}{\partial x} + \frac{\partial \sigma_{yz}}{\partial y} + \frac{\partial \sigma_{zz}}{\partial z} = \rho \frac{\partial^2 W}{\partial t^2}$$

Where:
U, V, W are components of displacement
$\rho$ is density of media
$\sigma_{ij}$ are components of stress tensor.

The pattern of stresses must be related to a pattern of strain. This relationship for incompressible media (e.g. tissues or other water based systems) is given by the following equations:

$$\sigma_{xx} = P + 2\mu E_{xx} \quad \sigma_{yy} = P + 2\mu E_{yy} \quad \sigma_{zz} = P + 2\mu E_{zz} \quad (2)$$
$$\sigma_{xy} = 2\mu E_{xy} \quad \sigma_{xz} = 2\mu E_{xz} \quad \sigma_{yz} = 2\mu E_{yz}$$

where $$\mu = \frac{E}{2(1+\nu)}, \nu = 0.5 \text{ is Poisson's ratio, } E \text{ is Young's Modulus, and}$$

$$E_{xx} = \frac{\partial U}{\partial x} \quad E_{yy} = \frac{\partial V}{\partial y} \quad E_{zz} = \frac{\partial W}{\partial z}$$

$$E_{xy} = \frac{1}{2}\left(\frac{\partial U}{\partial y} + \frac{\partial V}{\partial x}\right)$$

$$E_{xz} = \frac{1}{2}\left(\frac{\partial U}{\partial x} + \frac{\partial W}{\partial z}\right)$$

$$E_{yz} = \frac{1}{2}\left(\frac{\partial V}{\partial z} + \frac{\partial W}{\partial y}\right)$$

By combining equations (1) and (2), we can obtain three equations containing only three unknowns, U, V, W, which are components of displacement plus the unknown With the foregoing and other objects, advantages and features of the invention that will become hereinafter apparent, the nature of the invention may be more clearly understood by reference to the following detailed description of the invention, the appended claims and the several views illustrated in the drawings.

BRIEF DESCRIPTION OF THE DRAWINGS

FIG. 1 is a schematic representation of a model of soft "tissue" illustrating a device for loading incorporating pressure sensors used in the present invention;

FIG. 2 is the device of FIG. 1 after loading the tissue, and illustrating a typical pressure curve across a surface of the tissue;

FIG. 3 is similar to the tissue compression in FIG. 2, illustrating the effect of a presence of a tumor in the tissue;

FIG. 4 is an illustration of the structure shown in FIG. 3, with a piston deforming tissue from a side opposite from the pressure plate;

FIG. 14 illusrates a section of tissue being held against a support plate wherein a roller can be rolled along a pad directly applying deformation forces to the section of tissue;

FIG. 14A is a graphical representation of the moved stress curve in a X-axis direction with a hardened area or tumor being moved by the roller of FIG. 14;

FIG. 21A is a detailed sectional side view of the roller motion control system of the mechanical scanning unit shown in FIG. 20;

FIG. 21B is a detailed front view of the roller motion control system of the mechanical scanning unit shown in FIG. 20;

FIG. 22A is a front view of the indenter motion control system of the mechanical scanning unit;

FIG. 22B is a detailed sectional side view of the indenter motion control system of the mechanical scanning unit, as in FIG. 22A; and FIGS. 23A–C are enlarged fragmentary views of the indenter and its motion controlling cables shown in FIGS. 22A and B.

DETAILED DESCRIPTION OF THE INVENTION

Figure 5:
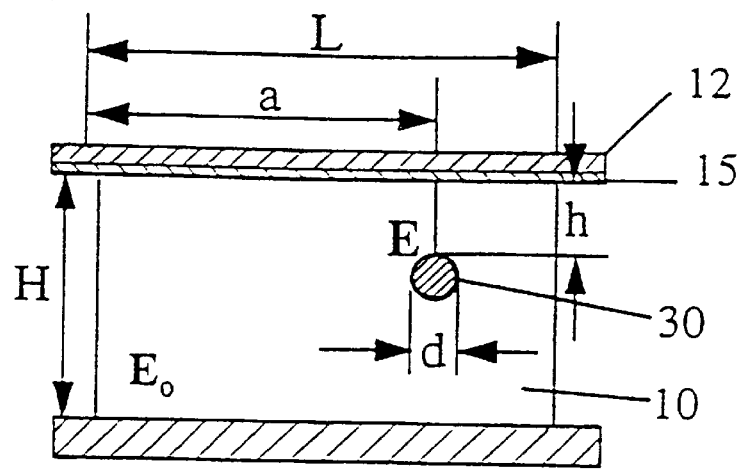
FIG. 5 is a schematic illustration of loading parameters for a model tissue being examined and a tumor in such tissue.

Referring now to the drawings, like elements are designated by like numerals. FIG. 1 illustrates a portion of a soft tissue 10 that is supported on a base 11 and which supports a flat rigid plate 12 capable of exerting pressure thereon from a force generator 13. A series of individual pressure sensors indicated at 15 are provided on the bottom surface of the plate 12 to sense pressure in an array across the surface of tissue 10.

FIG. 2 represents a pressure profile P(X) of the homogeneous tissue when deformed. FIG. 3 illustrates a homogeneous tissue pressure profile in the dotted line and the profile of tissue having an inclusion 18 in the solid line. The difference between these two pressure profiles shown in FIG. 3 provides information on the presence, location, and relative elasticity of inclusion 18 with respect to surrounding tissue 10. The strain pattern on the surface of the tissue 10 as shown in FIG. 3 is in this case represented in the form of pressure profile P(X). This strain pattern depends on the presence of an inclusion 18, as well as on the dimension of the tissue 10, neighboring anatomical features of that tissue, such as presence of a bone, and on the geometrical relationship of the tissue portion 10, support member 11 and deformation member 12. Therefore, the difference between the measured profile P(X) and the profile $P_o(x)$, shown by the dotted line, theoretically calculated for a homogenous model of that tissue under the same boundary conditions, contains direct information on the inclusion, rather than the strain profile P(X) itself.

FIG. 4 schematically illustrates how the present invention enhances the amplitude of the pressure profile and, thus, improves detection of an inclusion. In this instance, the tissue 10 is supported on a base 11, and a schematically shown piston or block 24 which also is called a "finger" as used in palpation, is provided on the base and is caused to protrude into the tissue and compress the tissue in a localized area indicated at 26 directly below inclusion 18, which can be a tumor.

The represented pressure profile schematically disposed on the top of the pressure plate 12 (which is displaced the same as that previously explained) represents the data provided by the pressure sensors 15. P(X) is represented as a dashed line and is the profile substantially as that shown in FIG. 3. P*(X), indicated by line 28, represents the pressure profile resulting from the presence of the piston 24 directly under the tumor. The piston 24 acts like a probe to cause extra compression in the desired region (e.g., inclusion 18) in addition to the general compression of the tissue 10 between plate 12 and base 11. This results in a substantial increase in the pressure profile P@(x) which reaches a maximum at $P^*_{max}$ directly over the tumor. By comparing the respective pressure profiles P(X) and P*(X), one can recognize that a much greater amplitude of the pressure profile can be obtained from the pressure sensors (to indicate an abnormality) when a probe (e.g., piston 24) or other extra compressive force is directed in the region of a tumor. In this case, a change in the pressure profile amplitude because of the piston 24 is represented as $\Delta p^*=P-P$.

FIGS. 5–9 are schematic examples to illustrate the applicability of the theory to the methods and devices disclosed, and to show the range of variables and measured parameters available for calculating meaningful values for quantitative analysis and evaluation. The illustrations of tissue are not meant to represent any particular portion of a human body.

Figure 5A:
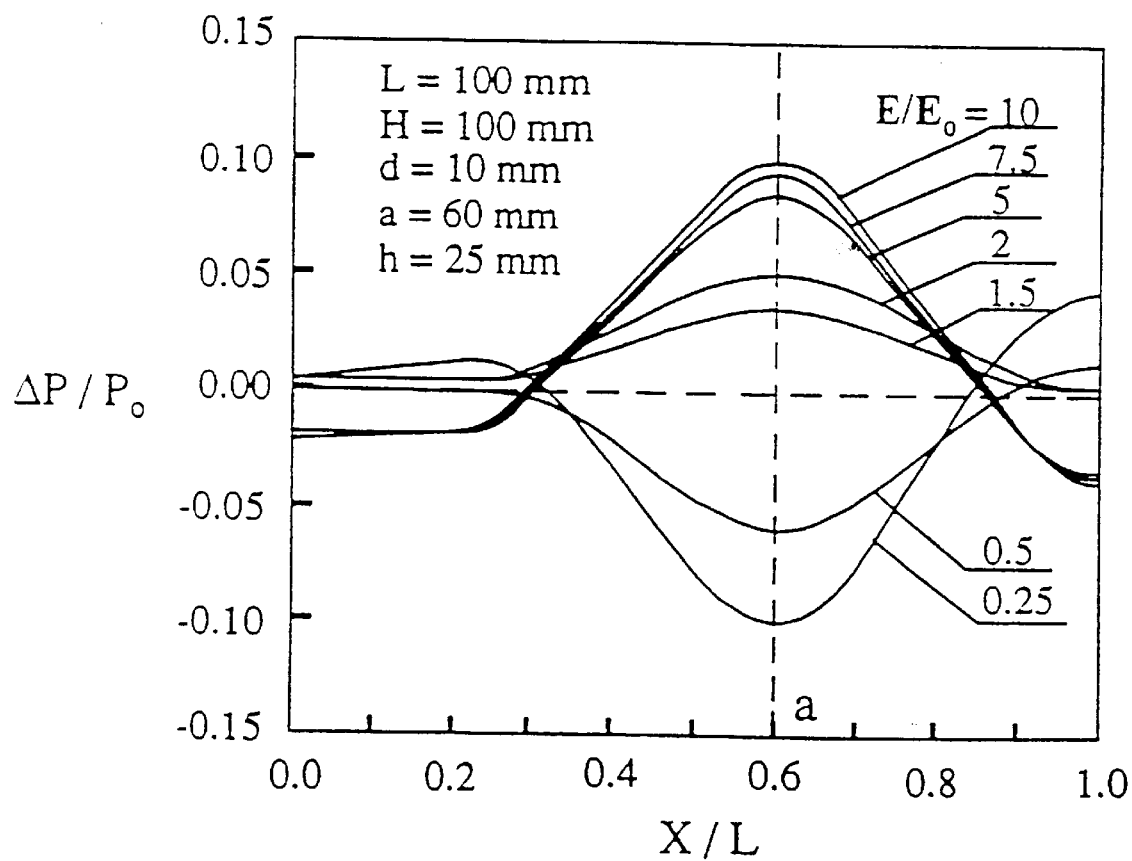
FIG. 5A is a plot of calculated pressure relationships across the surface at differing ratios of moduli of elasticity ratio between surrounding tissue and a tumor.

In FIG. 5, a schematic representation illustrates tissue having a tumor therein of a certain size and location. The graph of FIG. 5A illustrates a particular calculated differential pressure ratio as a function of the distance along the horizontal axis on the surface of the tissue. The graph is based on the dimensions shown in FIG. 5 having certain values, such as those listed in FIG. 5A. The symbol (E) represents the elasticity modulus (Young's modulus) of the tumor and ($E_o$) represents the elasticity modulus (Young's modulus) of the surrounding tissue. A ratio of these two moduli of elasticity ($E/E_o$) provides an indication of the hardness of the tumor relative to the surrounding tissue.

It is known that the Young's or shear elasticity modulus of a tumor varies significantly from the modulus of elasticity for surrounding tissue. For example, carcinoma may have an elasticity modulus of 10 times the elasticity modulus of normal tissue. However, in some cases, the elasticity modulus of tumors may not be substantially different from that of normal tissue making the tumors "nonpalpable". FIGS. 5 and 5A illustrate that the differential pressure profile ratio, namely ( $P/P_o$ ), (a change in amplitude of the pressure sensed at an inclusion divided by the pressure in that region of normal tissue) in the region surrounding the tumor is quite sensitive to changes in the elasticity modulus ratio ($E/E_o$).

In FIG. 5, a "block" of tissue 10 has a height H from a base to the contact point with the pressure sensors 15, and has a length L extending along the "X" direction (i.e., horizontal axis). A tumor 30 is positioned in the tissue 10, and is located a distance below the loading plate 12 equal to (h) and it has a diameter (d). Tumor 30 is located along the horizontal axis at a distance (a) from a left edge of the tissue 10.

FIG. 5A is a graph illustrating the differential pressure ratio ($\Delta P/P_o$) (values shown on the vertical axis), as a function of the distance along the X axis from the left edge of the tissue 10 to the right. The position of the tumor 30 at (a) is indicated by a vertical dotted line in FIG. 5A. Several plots of ( $P/P_o$ ) as a function of (X/L) are shown, each corresponding to a given ratio of moduli of elasticity ($E/E_o$), which indicates the relative hardness between a tumor and normal tissue.

With the parameters having the values shown in FIG. 5A, the plots illustrate that a tumor/tissue combination having an elasticity moduli ratio ($E/E_o$) of only 1.5, i.e., the tumor having a modulus of elasticity of 1.5 times that of the surrounding tissue, a detectable change in the pressure signal of about 3% is observed for the region surrounding the tumor. This means that even tumors that are not much harder than surrounding tissue can be detected quite easily. It is known that a tumor in a breast, for example, can be detected by a palpation (which is the only technique available for evaluating elasticity), but palpation is reliable only when the tumor has progressed so its Young's modulus is more than five to ten times larger than that of surrounding tissue. The differential pressure signal ($\Delta P/P_o$) shows a more pronounced effect near the tumor when the elasticity moduli ratio ($E/E_o$) is 2 or 5 or more. However, in this case when the elasticity moduli ratio is greater than 7.5 (e.g., 10), there is not a substantial increase in the differential pressure profile above that shown for $E/E_o=7.5$. When tumors or inclusions are softer than the surrounding tissue, e.g., the ratio ($E/E_o$) is 0.5, a substantial difference in the differential pressure profile ($\Delta P/P_o$) in the region of the tumor is readily observable. A more pronounced effect occurs when the ratio ($E/E_o$) is 0.25. Accordingly, by observing a relatively small change in the pressure profile (only 2–10), one can detect tumors that have a relatively small change in the modulus of elasticity. This clinically significant data is obtained by using a pressure sensor array extending across the surface of the tissue and external to the tissue that measures a pressure profile response during compression of the tissue.

Figure 6:
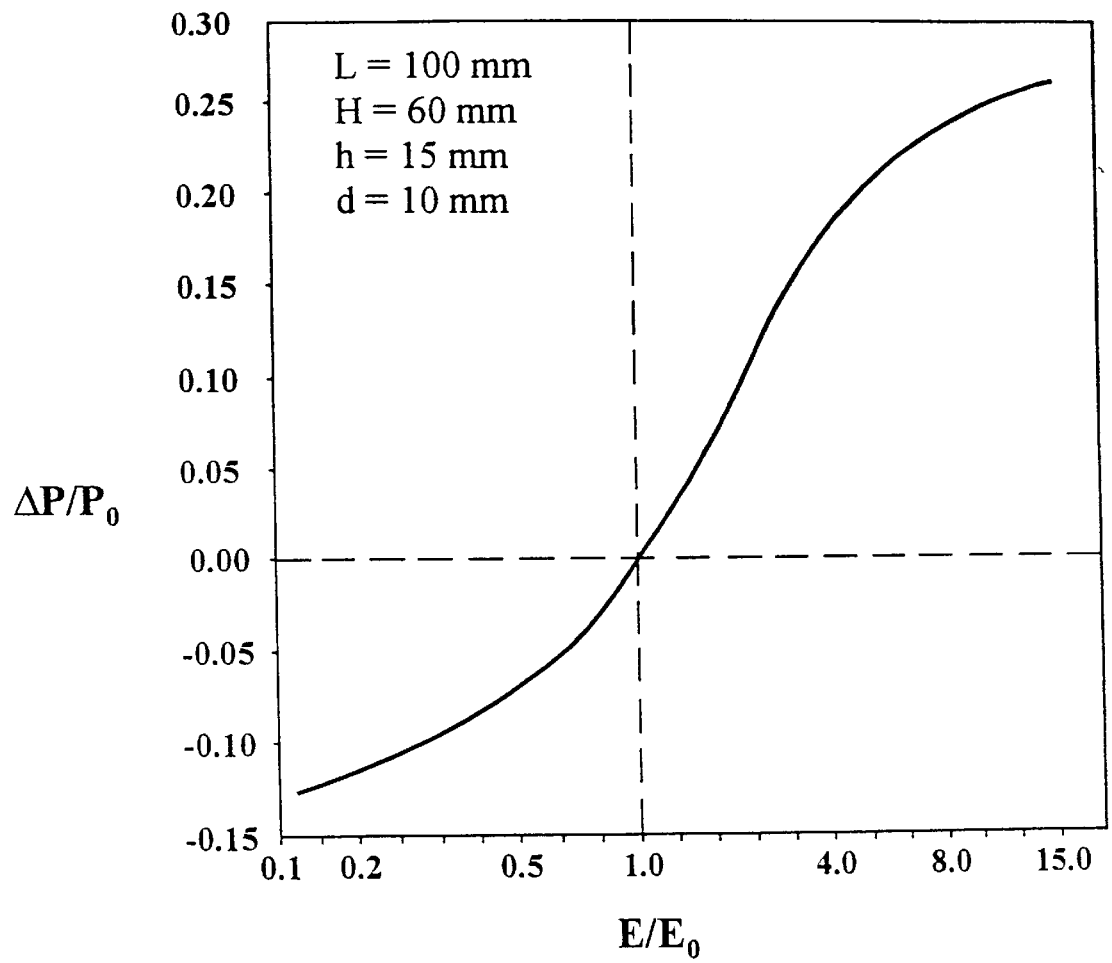
FIG. 6 is a graphical representation of the calculated relationship between pressure ratios and moduli of elasticity ratios for a loading structure shown in FIG. 5.

FIG. 6 illustrates the changes in pressure sensed as a function of the change in the elasticity modulus ratio ($E/E_o$).

Similar to the illustration in FIGS. 5 and 5A, FIG. 6 shows that easily achievable resolution of a few percent in the pressure profile ratio ($\Delta P/P_o$) can enable one to detect inclusions differing from the surrounding tissue in hardness to an extent which does not permit palpatory detection. The graph is based on a tissue block 10 having the parameters such as indicated on FIG. 6. The values on the horizontal axis ($E/E_o$) are provided on a logarithmic basis to facilitate comparison purposes.

Figure 7:
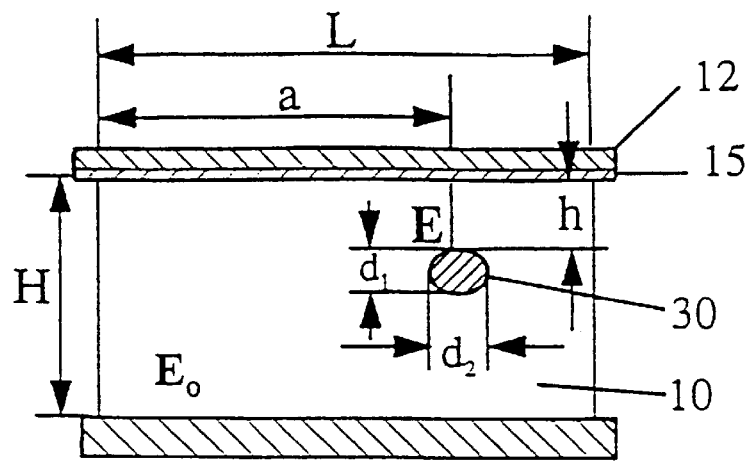
FIG. 7 is a schematic representation similar to that shown in FIG. 5 with certain loading parameters illustrated.
Figure 7A:
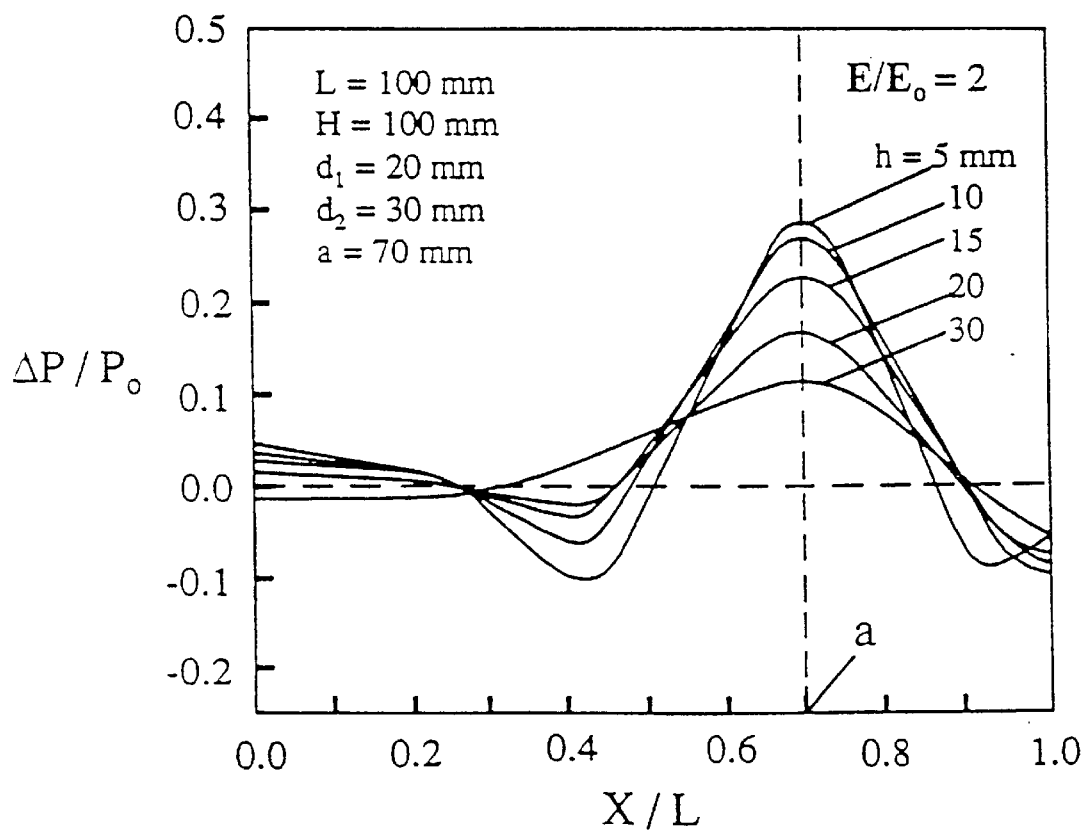
FIG. 7A is a graphical representation of the calculated pressure relationships across the surface at differing depths of a tumor in tissue shown in FIG. 7.

FIGS. 7 and 7A illustrate that the capability to detect a tumor within a block of tissue depends on the distance of the tumor from the tissue surface (skin) and pressure sensors. As seen in FIG. 7, the block of tissue 10 has a tumor 30 located therein and, in this instance, the vertical height of the tumor is represented as $d_1$, and the lateral width of tumor is represented as $d_2$. The parameter (a) represents the tumor's distance from its position from the left side of the tissue block. A set of values for the dimensions shown in FIG. 7 are listed in FIG. 7A. FIG. 7A shows the calculated plot of the pressure profile ratio ($\Delta P/P_o$) (the change in pressure of tumor tissue relative to normal tissue divided by the pressure sensed with no tumor) as a function of (X/L) along the X axis. This graph illustrates that a substantial change in the pressure profile ratio ($\Delta P/P_o$) of about 0.3 is observed when the tumor is a small distance (h=5 or 10 mm) from the tissue surface and that a smaller change in pressure profile ratio occurs when the tumor is far from the surface (e.g., h=30 mm). However, even when the tumor is deep (h=30 mm), the pressure profile ratio change is still readily discernible (with $\Delta P/P_o$ about 0.1 which is quite measurable) to indicate a tissue abnormality at about X/L=0.70. The ratio of ($E/E_o$) is taken to be equal to 2.

Figure 8:
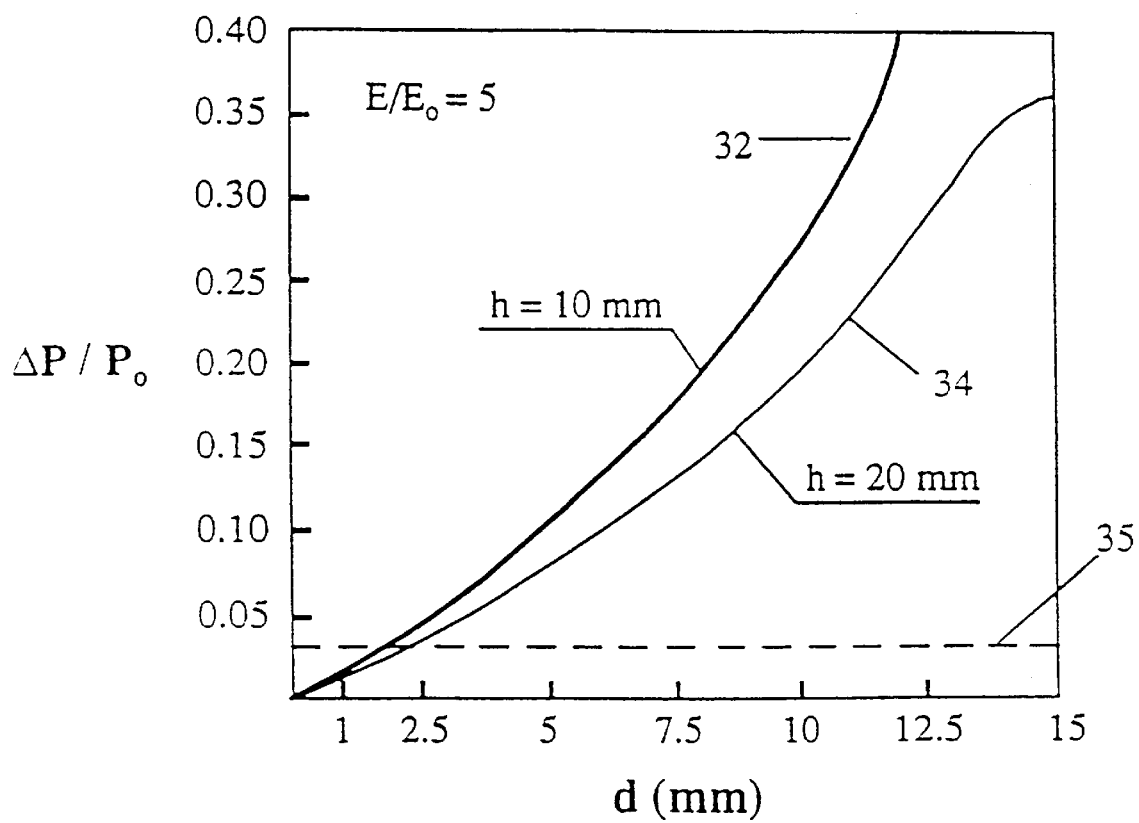
FIG. 8 is agcal representation of calculated pressure relationships relative to the diameter of a tumor being sensed at differing depth of the tumor as shown in FIG. 5.

FIG. 8 illustrates the effect on the ability to ascertain a change in pressure with the sensors 15 as a function of the change in the diameter d of the tumor 30. As seen in FIG. 8, the elasticity moduli ratio ($E/E_o$) is equal to five, and the graph shows a plot of ($\Delta P/P_o$) versus d for a tumor with h=10 mm (indicated by line 32) and a tumor with h=20 mm (indicated by line 34). The pressure ratio ($\Delta P/P_o$) at the point of surface above the tumor, is indicated along the vertical axis, while the diameter of the tumor d is indicated along the horizontal axis.

The reference line indicated as 35 is more or less the base line for sensitivity of the ratio ($\Delta P/P_o$) measurement that can be easily obtained with existing pressure sensors. An error of about one percent in pressure sensors is quite common, even with very miniature sensors, and the base line 35 represents a change of about three percent, which will give a clear indication of the presence of a tumor in normal tissue having a diameter (d) in the range of one to two millimeters. FIG. 8 indicates that, the larger the tumor, the greater is the change in the pressure ratio.

Figure 9:
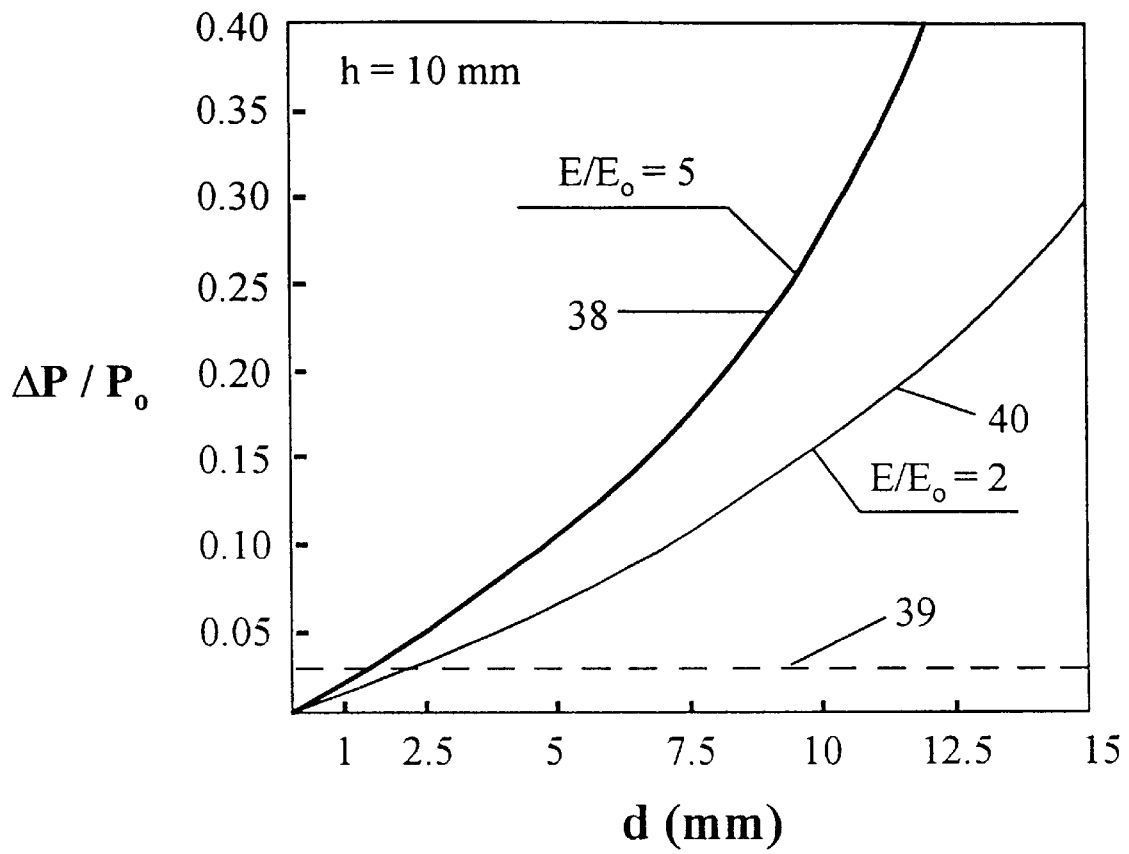
FIG. 9 is a graphical representation of the calculated pressure relationships relative to the diameter of a tumor, at differing ratios of moduli of elasticity between the surrounding tissue and the tumor.

FIG. 9 again illustrates the change in the pressure profile ratio ($\Delta P/P_o$) at the point of surface above the tumor as a function of the diameter (d) of the tumor. However, this time, the depth (h) of the tumor below the sensors 15 is set at 10 mm and a plot is provided for the case when the elasticity moduli ratio ($E/E_o$) equals 5 (indicated by upper curve 38) and when ($E/E_o$) equals 2 (indicated by lower curve 40). As expected, the greater the difference in the elasticity modulus between the tumor and surrounding tissue, (a larger ratio ($E/E_o$)), the more substantial change in the pressure profile ratio ($\Delta P/P_o$) for a given diameter tumor and the more easily the tumor will be detected. Taking the ratio ($\Delta P/P_o$) as an indication of sensitivity, one can observe line ($E/E_o$=5) crossing a threshold level of sensitivity (indicated by the dashed line at 39) indicating that detection of a tumor in the range of 1 mm can be made. When an elasticity modulus ratio is 2 (curve 40), one can observe that a tumor of 2.5 mm in diameter (d) could be detected. It is well known that palpation permits detection of tumors only if their diameter is over 8–10 mm, but not smaller. The graph in FIG. 9 shows quantitatively how the detection device (pressure sensors) becomes substantially more sensitive (on a relative basis, i.e., a larger change in the pressure profile ratio ($\Delta P/P_o$) is observed) as the elasticity moduli ratio ($E/E_o$) of the tumor tissue relative to the normal tissue increases.

Figure 10:
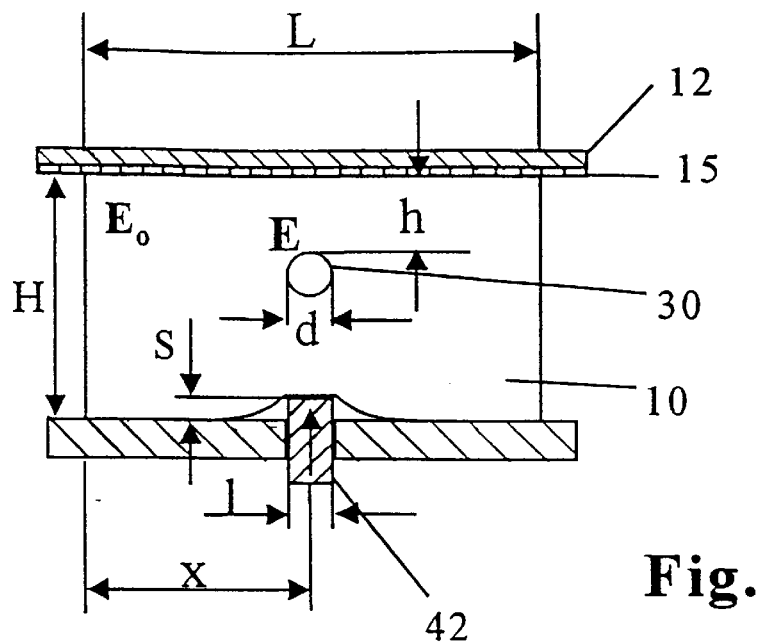
FIG. 10 is a schematic representation of a block of tissue having a tumor therein with a "finger" inserted from a side opposite to a loading plate.
Figure 10A:
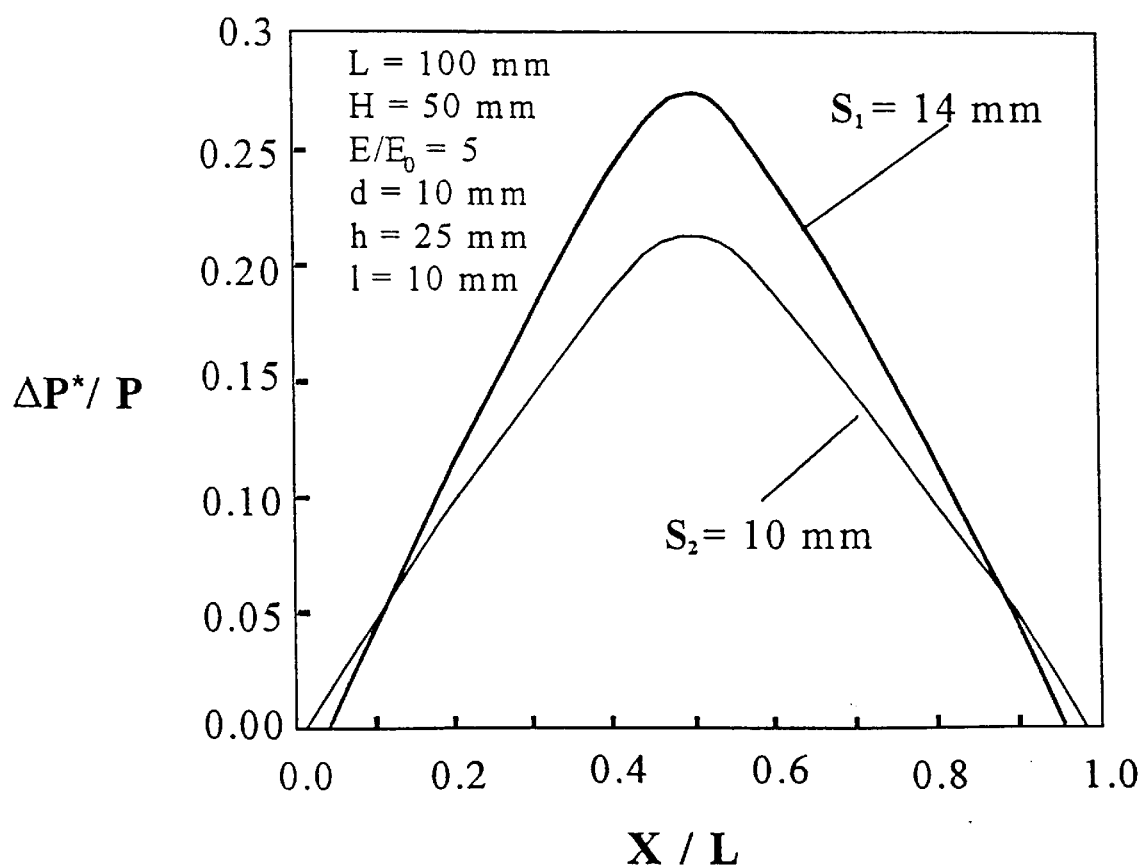
FIG. 10A is a graphical representation related to FIG. 10 illustrating an increase of the resolution of the pressure relationship across the surface relative to position at two different depths of the probe illustrated in FIG. 10.

FIGS. 10 and 10A illustrate the effects of measuring the pressure profile on tissue having an inclusion while providing a "finger" probe or a piston from an opposite side from the main support 12. The sensor array 15 is again in place on the support 12, and the tissue block 10 has tumor 30 located therein. The dimensional notations are the same as those previously used. In this form of the invention, however, a finger probe 42 is applied through the base support into the tissue block 10 as shown, and the penetration distance is labeled as (S). The finger probe is illustrated as being directly below the tumor 30, which has a diameter of (d). FIGS. 10 and 10A provide an example of the sensitivity on the pressure sensors when a finger probe or piston has been applied from an opposite side from the pressure sensing array 15. Taking standard dimensions as shown in FIG. 10A, and with an elasticity moduli ratio ($E/E_o$) of 5, and the diameter of the finger probe (1) as 10 mm, the graph reflects the differences in pressure sensed along the X axis.

In the graph of FIG. 10A, the horizontal axis is X/L, and the vertical axis is $\Delta P^*/P$. The plotted curve represents the pressure profile ratio ($\Delta P^*/P$) as a function of distance along a horizontal axis. When the finger probe or piston 42 has penetrated 10 mm (S=10), the graph is represented by a thin line, and when the probe has penetrated to S=14 mm, the graph represented by a thick line. This graph illustrates that the use of a finger probe, which simulates a probing human finger applied to tissue, accentuates the pressure profile differential in the location of the tumor, making the tumor even easier to detect than without the probe. The graph also illustrates that the greater the penetration (S=14 mm), the greater the pressure profile change (i.e., sensitivity), particularly near the center of the tumor.

Figure 11:
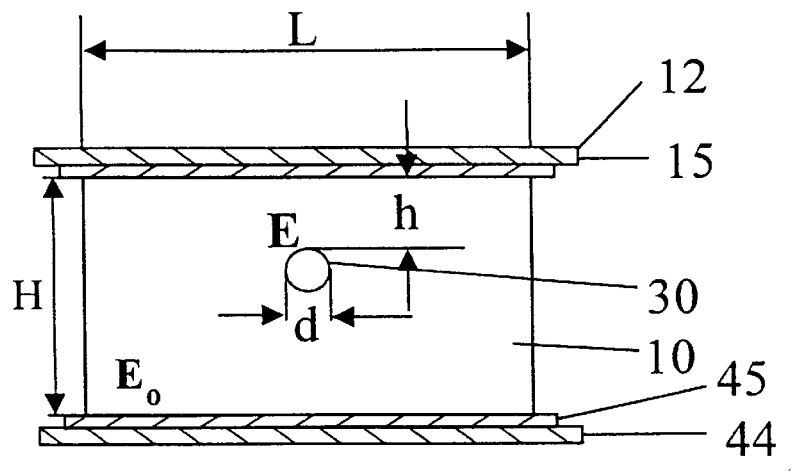
FIG. 11 is a graphical representation of a portion of tissue with pressure sensors on each of the loading plates.
Figure 11A:
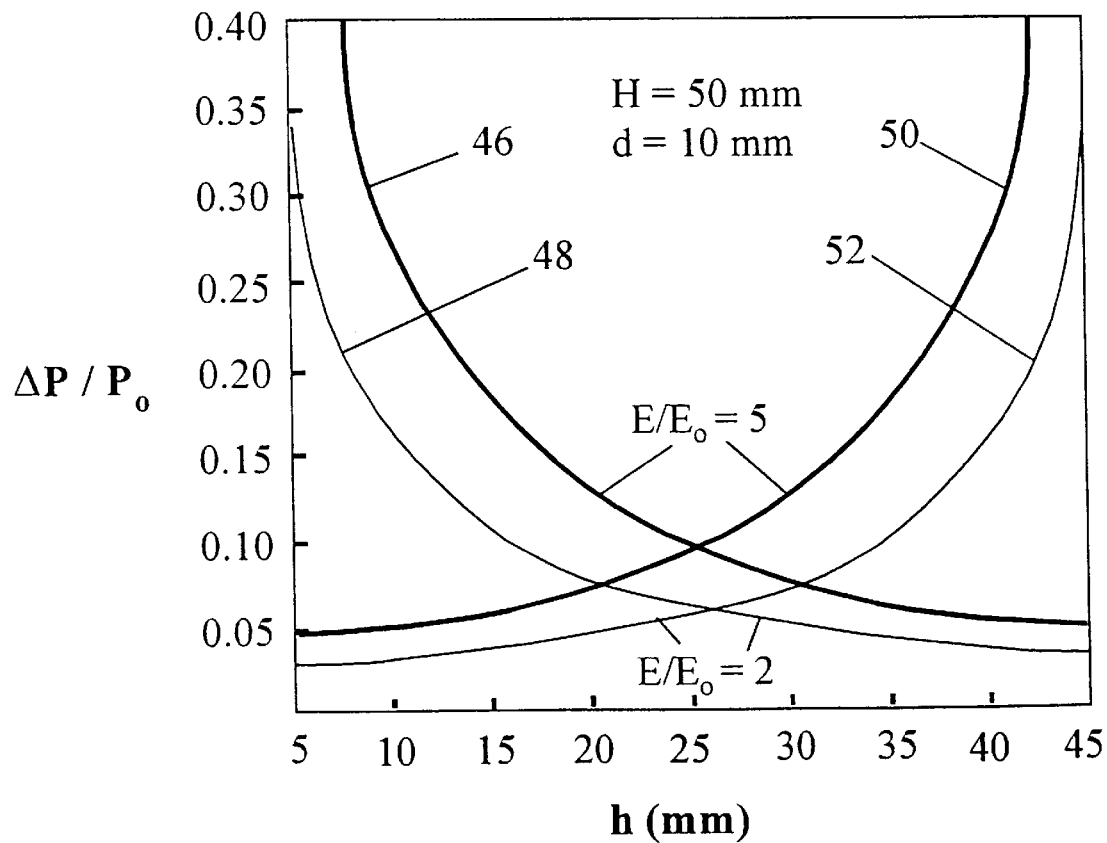
FIG. 11A is a graphical representation of the pressure relationships and sensitivity relative to the distance of a tumor from the sensors being used at differing ratios of moduli of elasticity between the surrounding tissue and the tumor.

FIGS. 11 and 11A illustrate that pressure profile sensitivity can be enhanced by having pressure sensor arrays on both sides of the tissue block. For example, the plate 12 and pressure array 15 would be on top of tissue 10, and a second plate 44 having a pressure array 45 thereon is below and supporting tissue 10. As in the previous illustrations and examples, the block of tissue 10 with the tumor 30 therein will be compressed a desired amount. The dimensional notations are also as shown before. The graph of FIG. 11A illustrates the pressure profile ratio ($\Delta P/P_o$) at the point of surface above the tumor (i.e., sensitivity) change as a function of the height h, which is the distance from the top of the tumor 30 to the upper pressure array 15. The height H of the tissue block is a nominal 50 mm and the tumor has a diameter (d) of 10 mm.

Calculated values show a decrease in the sensitivity of pressure changes measured by the top pressure array 15 as h increases (from 5 to 45 mm). Plots 46 and 48 illustrate a decrease in measuring pressure sensitivity the further the tumor is away from the upper pressure array 15. Similarly, the plots 50 and 52, respectively, show the increase in sensitivity for detection of a tumor at the bottom pressure arrays 45 when the tumor is closer to the pressure array 45. For the bottom sensor array plots 50 and 52, the elasticity moduli ratio ($E/E_o$) is 5 for line 50 and the elasticity moduli ratio is 2 for line 52. Accordingly, when the sensitivity of a single pressure array decreases because the tumor is far from the tissue block surface, one can compensate by adding a second pressure sensor array so that a pressure sensor array is on each side of the tissue block being sensed.

Figure 12:
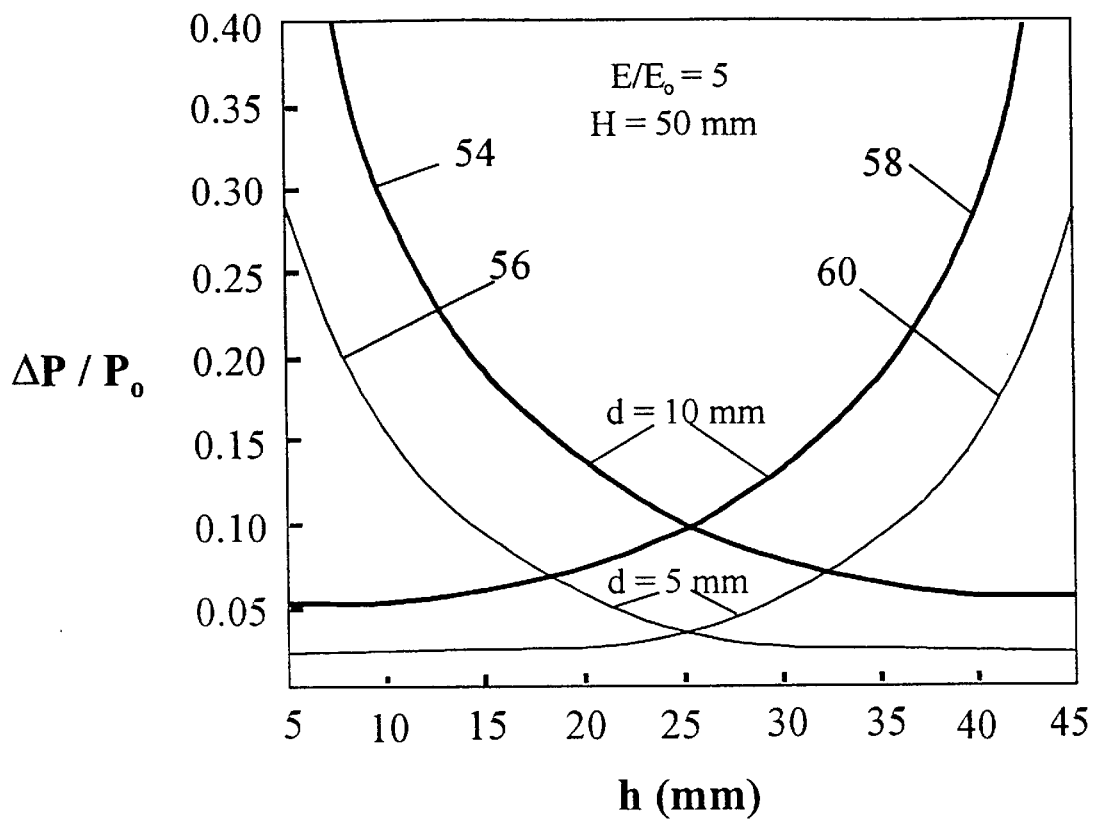
FIG. 12 is a graphical representation illustrating the sensitivity to the depth of a tumor as related to the size of the tumor as shown in FIG. 11.

FIG. 12 illustrates essentially the same conditions as shown in FIGS. 11 and 11A. However, FIG. 12 illustrates this effect for a single elasticity moduli ratio ($E/E_o$=5 ) but with two different tumor diameters (d=10 mm and d=5 mm). In FIG. 12, the curve corresponding to the pressure sensed by the pressure sensing array 15 is illustrated by curves 54 and 56, and it shows the pressure sensed decreasing as h (the distance between the tumor and array 15) increases. The curve 56 illustrates this relationship with the tumor having a diameter (d) of 5 mm and curve 54 corresponds to the tumor having a diameter (d) of 10 mm.

Curve 58 illustrates the sensitivity of the bottom pressure sensing array 45 (FIG. 11) with a diameter of the tumor at 10 mm and the curve 60 illustrates the sensitivity at the array 45 with the tumor having a diameter of 5 mm. As expected, FIG. 12 shows that a greater pressure change is sensed for larger diameter tumors. Moreover, as the distance of the tumor from the upper array 15 increases resulting in lower measuring sensitivity from the top, the distance between the tumor and bottom array 45 decreases resulting in higher measuring sensitivity from the bottom.

From the illustrations of FIGS. 11, 11A, and 12, it can be seen that the use of two pressure sensing arrays on opposite sides of the supported tissue block 10 provides an opportunity for better detection of tumors farther from the tissue block surface.

Figure 13A:
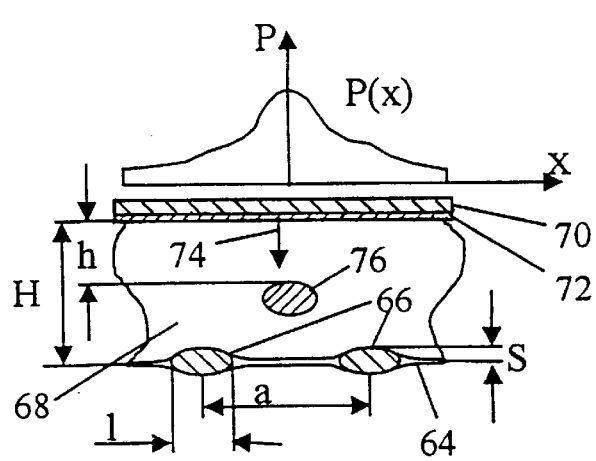
FIG. 13A is a graphical representation of tissue positioned over underlying objects such as ribs, and being loaded in accordance with the present invention.
Figure 13B:
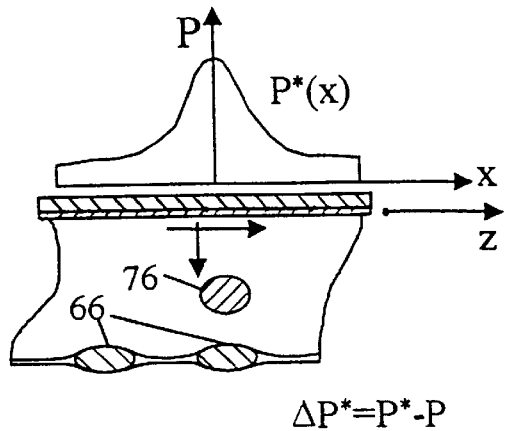
FIG. 13B is an illustration similar to that shown in FIG. 13A with the outer surface of the tissue shifted relative to the supporting ribs.
Figure 13C:
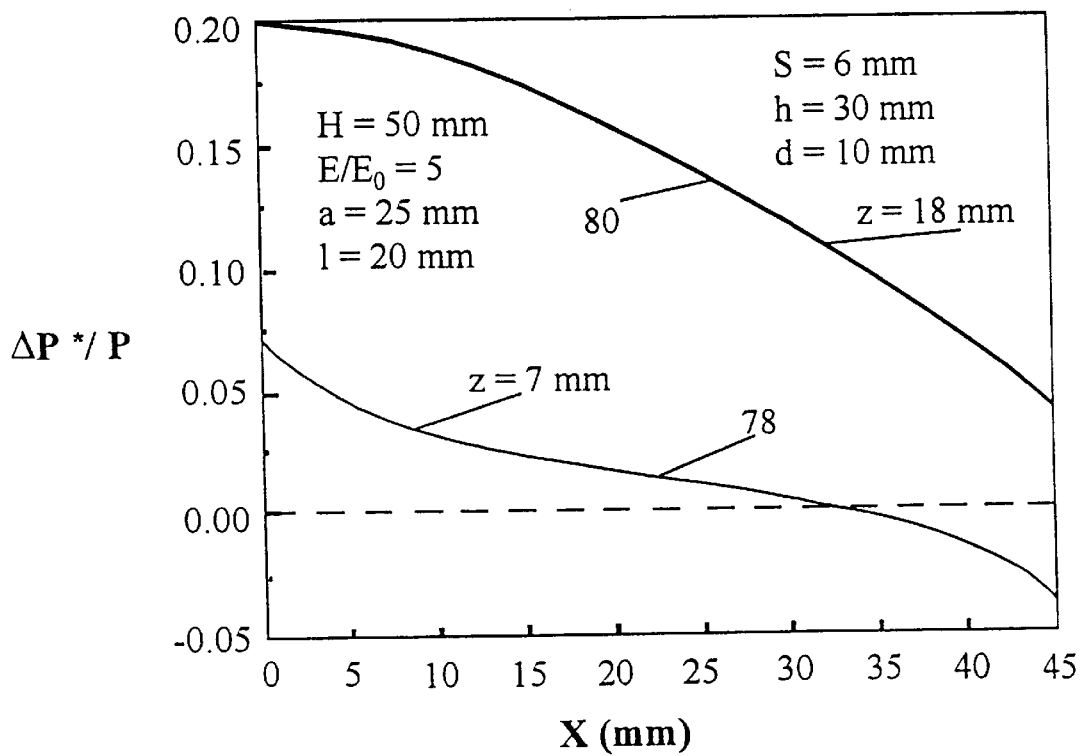
FIG. 13C is a graphical representation of the changes in pressure profile after a shift of the outer surface of the tissue has been made as shown in FIG. 13B.

FIGS. 13A and 13B illustrate a tumor in tissue located on the chest adjacent to ribs, and FIGS. 13B and 13C illustrate that shifting of the pressure sensor while contacting the tissue accentuates sensitivity of detection for the tumor.

In FIG. 13A, a rib cage 64 is illustrated schematically as having two ribs 66 shown in cross-section and held adjacent to each other with normal connective tissue. A quantity of tissue, such as breast tissue, is indicated at 68 and is positioned between the ribs and an outer surface of the tissue, against which a pressure plate 70 is placed, which has a pressure array 72 thereunder. Force is applied as indicated by the arrow 74 in FIG. 13A. A tumor 76 is located adjacent to and midway between the ribs 66. The distance between the centers of the ribs is indicated as (a), and the width of the ribs is indicated as (l). The height of each rib above the general support plane of the tissue is indicated by (S). The profile of pressure sensed by an array 72 is indicated at the top of FIG. 13A, with the maximum pressure detected corresponding to a position directly above the tumor 76.

In a laterally shifted position as shown in FIG. 13B, the pressure plate 70 has been shifted relative to the ribs 66. This tends to move the tumor 76 closer to one of the ribs, as shown. The tumor is now in a position where it is very near or substantially over a rib. This changed positioning of the tumor is reflected by the substantial increase in the peak of pressure profile illustrated at the top of FIG. 13B. In this case, a change in the pressure profile because of the lateral shift is represented as $\Delta P^* = P^* 31\ P$. The lateral shift of the pressure plate 70 and pressure sensor 72 can be measured from a starting value. Although a lateral shift occurs in the X direction, the amount of shift will be indicated by "Z" in FIG. 13C. The increase of pressure sensitivity ($\Delta P^*/P$) is marked on the vertical axis, and the horizontal axis indicates an X dimension, which has a zero point at the peak pressure in FIG. 13B.

The graph of FIG. 13C calculated with the use of the mathematical approach described above illustrates the change in pressure profile ($\Delta P^*/P$) (after a lateral shift of the pressure plate 70) as a function of the distance X laterally away from the center of the pressure profile peak for $P^*(x)$. Plot 78 illustrates this relationship for a lateral shift of 7 mm of the pressure plate relative to the stationary rib cage (the difference shown between FIGS. 13A and 13B), and plot 80 corresponds to a lateral shift of 18 mm.

In this example, the distance between the center of the ribs (a) is 25 mm and (l), which is the width of the rib, is 20 mm. The other dimensional parameters are illustrated at FIG. 13C. The graphs indicate that a greater pressure measuring sensitivity is achieved in detecting a tumor in a breast (or other tissue) when the pressure plate is shifted laterally while in contact with the tissue. This is particularly true when the underlying tissue includes a bony structure such as ribs which are adjacent the tumor and over which the tumor will be moved during the shift. elasticities of these structures using the data on pressure variations across an array. The pressure sensor array can be on both sides of the tissue.

Figure 15:
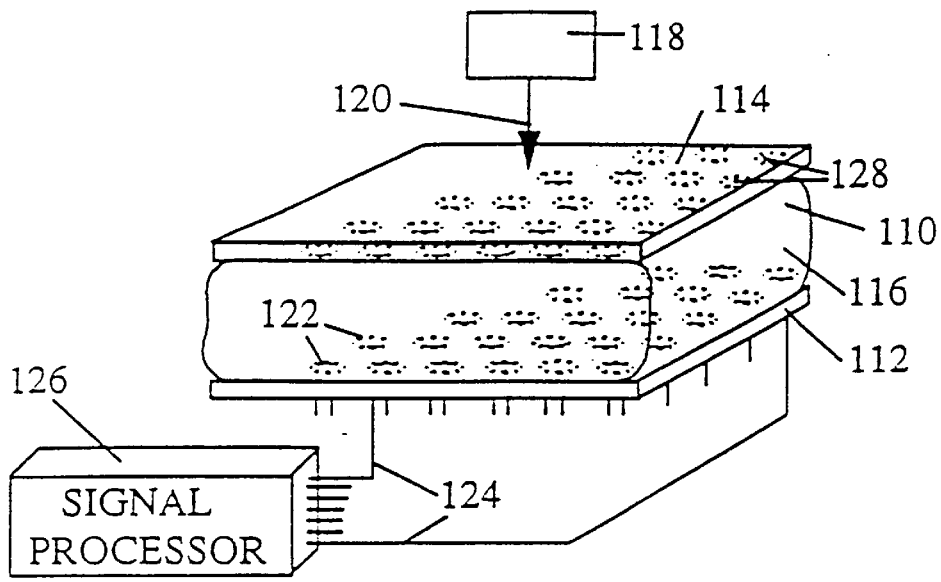
FIG. 15 is a schematic representational view of force-applying plates similar to that shown in FIG. 5 or FIG. 11 having an array of sensors thereon on at least one of the plates.
Figure 16:
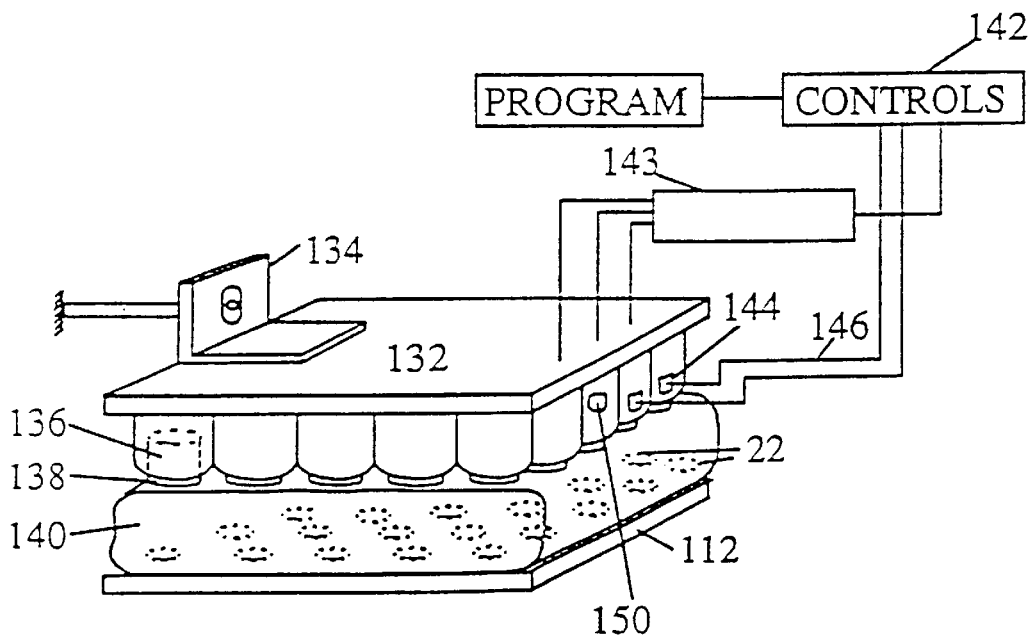
FIG. 16 is a schematic representation of a multiplicity of individual actuators compressing a portion of tissue against a reaction plate having an array of pressure or force sensors.

FIG. 16 illustrates a variation of the device of FIG. 15, and can include the same type of a backing plate 112, but in this instance the plate 114 and load member 118 are replaced by a backing plate 132 which can be adjustably fixed in spaced relation to the support plate 112, for example, by an adjustable bracket 134. The plate 132 has a number of individual fluid pressure actuators 136 mounted thereon in an array, and as shown, they are closely spaced. Each of the actuators is formed with a piston on the interior of a cylinder, and each piston has an outer rod portion 138 that has an end surface engaging tissue (indicated at 140) which is supported on the plate 112. The individual actuators 136 have controls 142 controlling suitable servovalves 143 to, in turn, control the fluid pressure in each of the actuators and thus to control the force applied in a local area by the end of the rod. A force feedback sensor indicated at 144 is provided to determine the force exerted by each actuator. Sensor 144 in turn provides a feedback signal along a line 146 to the controls 142 to indicate whether or not a pre-programmed force from a program for operation of each actuator is being met. These control systems for actuators are closed loop servosystems. Separate channels are used for each actuator and the pressure will be adjusted to equal the desired pressure. Closed loop servosystems generally use hydraulic actuators so that precise piston position, as well as the load can be obtained. The position of the rod ends 138, which form flat surfaces bearing on the tissue, can be sensed relative to the base plate 132 by using position sensors that can be internal of the actuators, that is, internally located within the cylinders, to sense the position of the respective pistons relative to the base plate 132. Such a sensor is illustrated schematically at 150 and will provide feedback signals to the controller 142 as well. The control of actuator position and/or force permits simulation of palpation by varying the force on each actuator to achieve the desired compression or displacement of underlying tissue.

Figure 17:
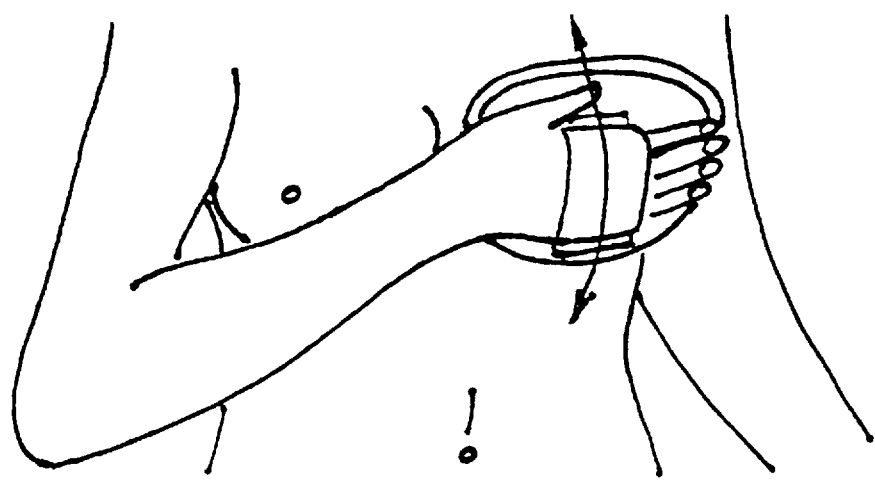
FIG. 17 is a schematic illustration of examination of a breast using a pad which incorporates a pressure sensing array in accordance with the present invention.

In an embodiment of a method and a device of the present invention shown in FIG. 17, the device is made in a form of a hand-held pad comprising a pressure sensor array and a microprocessor interfaced via a data acquisition circuit. The pad is pressed normally to the breast and is moved periodically in the direction perpendicular to the ribs as is shown in FIG. 17. Detection of a nodule is achieved by analyzing the dynamic and spatial features of the pressure pattern while the pressure sensing probe is periodically moved transversely to the ribs. A nodule within the breast that moves together with the surrounding tissue over the ribs produces additional periodic stress on the pressure sensing elements situated on the flat surface contacting the breast. The principle of detection of nodules is illustrated in FIGS. 13A, B, and C. The graph of FIG. 13C illustrates the change in pressure profile after a particular lateral shift of a probe. The graph clearly shows how significant the increase of the contribution of the tumor is in the pressure profile after a lateral shift (20% in this particular case). The ribs play a role as an amplifier of the "signal" from the tumor. Periodic movement of the probe across the ribs plus spatial periodicity of the ribs provide unique possibilities for filtering out the "signals" from targets other than lesions which are to be detected. This device will be able to detect objectively the presence of lumps in a breast and provide a warning signal. The result of examination is displayed in the form of a sound or light signal.

Figure 18A:
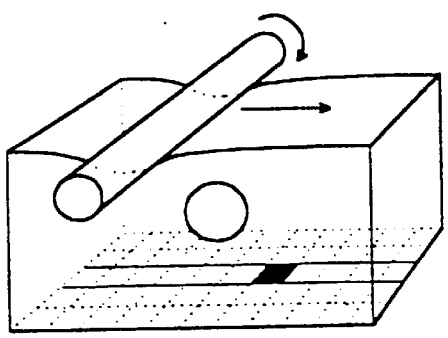
FIG. 18A is a perspective illustration of an experiment done with the use of a rubber model of a tissue with an inclusion therein.
Figure 18B:
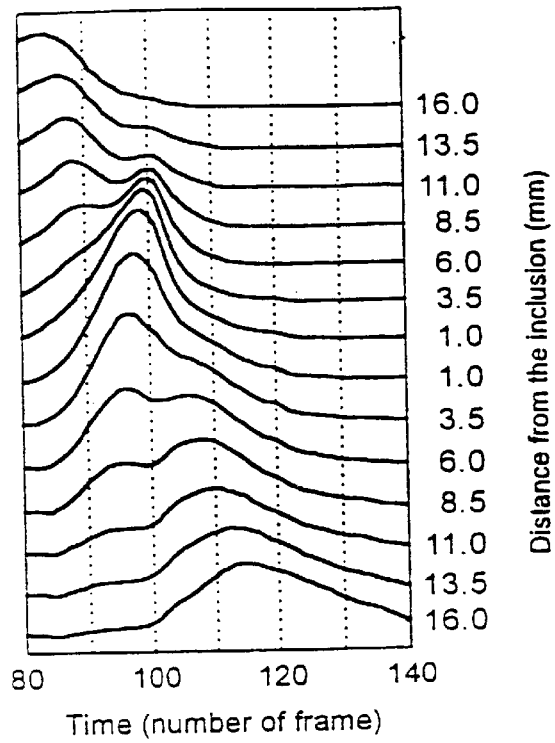
FIG. 18B is a plot of the pressure profiles obtained from the sensors situated at different distances from the inclusion using the experimental model shown in FIG. 18B.
Figure 18C:
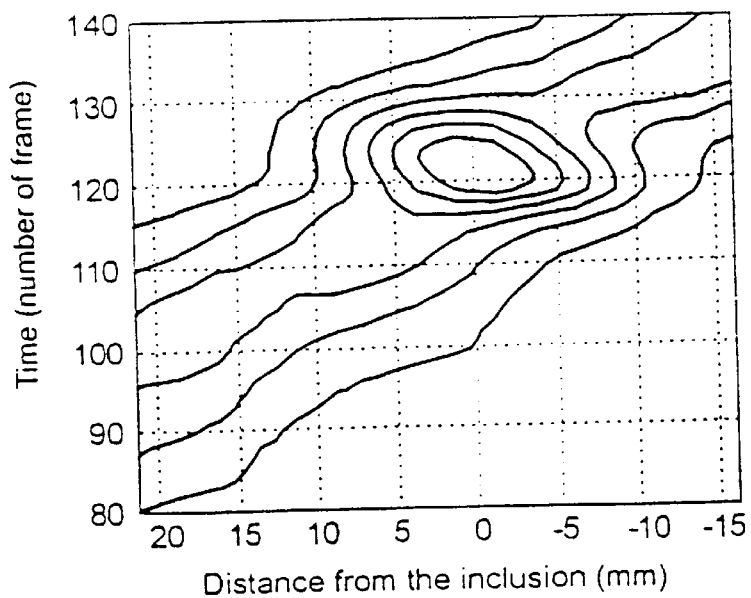
FIG. 18C is a topographic representation of the data shown in FIG. 18A.

FIGS. 18A, B, and C describe a model experiment illustrating the principle of detection of a nodule in the case when there is a relative motion of a linear support member (simulating a rib), in respect to the nodule and the pressure sensing array. FIG. 18A shows a rubber model 210 with dimensions 50×40×25 mm having in its center a hard inclusion 230 with diameter placed on a commercially available pressure sensor array 215 Tekscan I-SCAN 100 manufactured by Tekscan Inc., Boston, MA. The array 215 consists of conductive rows and columns whose intersecting points form sensing locations. The rows and columns are separated by a material which varies its electrical resistance with applied force, and thus each intersection becomes a force sensor. Sensors are schematically shown in FIG. 18A as squares at the lower surface of the model. A roller 294 made of a metal rod having a diameter of 15 mm was rolled over the model 210 and signals from the sensors along the row beneath the inclusion 230 (as shown in the FIG. 18A) were recorded in time. FIG. 18B shows pressure temporal profiles for the sensors situated at a different distance from the inclusion (the distance for each profile is given at the left side of the figure). One can clearly see how the profiles differ depending on the relative position of the sensor and the inclusion. A number of temporal and spatial features of the signal can be used to design an algorithm for detecting the presence of a nodule: the amplitude of the signal, the width of the peak, the shape of the pressure profile, etc. FIG. 18C shows the data of FIG. 18B as a topographic map with the clear image of the inclusion 230.

Figure 19:
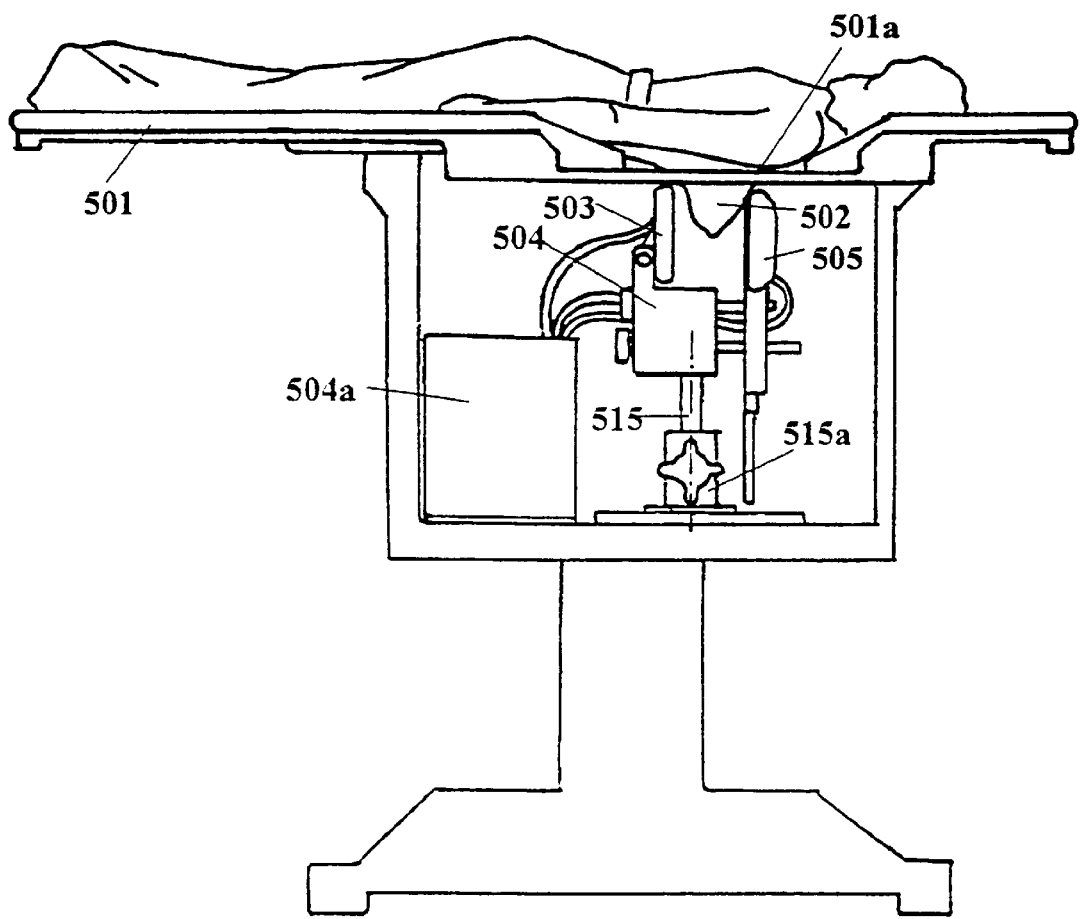
FIG. 19 is a front elevational view of clinical apparatus for performing mechanical imaging of a breast in accordance with the present invention.

Another embodiment of the invention shown in FIGS. 19–23 is a clinical device for imaging the mechanical structure of the examined breast and diagnosing diseases accompanied by changes in the elasticity of breast tissue. The overall view of the device for mechanical imaging of the breast is shown in FIG. 19. The patient lays face down on the table 501 so that the examined breast 502 is located and loosely inserted into the breast aperture 501a. Such an examination position allows the pectoral muscles to relax and the chest to expand into the breast aperture for greater access to the breast tissue adjacent to the chest wall. Inside the breast aperture, the breast is placed between the holder 505 of the mechanical scanning unit and the pressure sensor array 503, and consequently compressed. Both the support 504 of the pressure sensor array and the holder 505 of the scanning unit can rotate along the vertical axis with a revolving holder 515 in its positioning base 515a.

The signals from the pressure sensing elements of the pressure sensor array are buffered and multiplexed directly near the pressure sensor array. The lines conducting these multiplexed signals along with additional pressure signals, and positioning control signals are brought to the electronics compartment 504a where part of the microcomputer interface, pressure signal decoding, and motor driving circuitry is located. The entire system is controlled by an external CPU from a personal computer.

Figure 20:
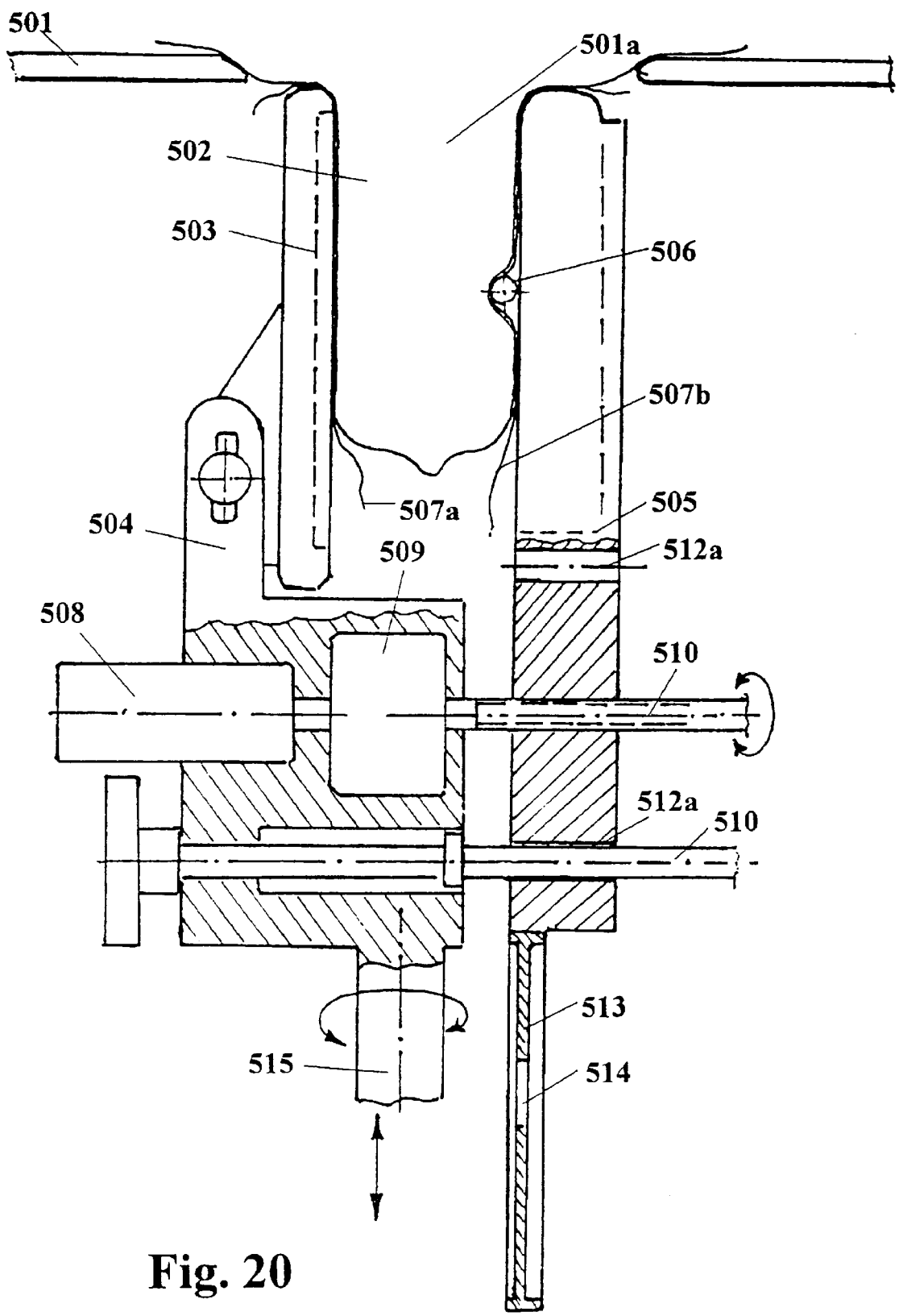
FIG. 20 is a sectional view of an embodiment of the mechanical scanning unit of the device shown in FIG. 19 and which employs a roller.

FIG. 20 shows the compression mechanism and positioning of the scanning unit and the pressure sensor. The motor 508 controls the level of breast compression through the reduction gear 509 and retractable screw rod 510. Pressure sensor array 503 is mounted on the support 504 which can rotate to the desired position with respect to the examined breast with the revolving holder 515. The holder 505 comprises transparent exchangeable plate 513 with biopsy window 514. When the scanning unit holder 505 is rotated by 180° around the screw rod 510 and fixed in the position by the fixing pin 511 in a fixing pin hole 512a, the exchangeable plate 513 is in the place of contact with the breast. The exchangeable plate contains a biopsy window 514 which may be situated in different parts of the exchangeable plate 513 to provide access to the target lesion in the breast to be reached by the aspiration needle or biopsy gun. Disposable polymer films 507a and b are replaced after each examination. The surface of the film 507b facing the dynamic pressure element (roller in this case) 506 is covered with a lubricant to decrease the friction while moving the pressure element over the breast. In a version of this embodiment, the pressure element is a roller moving in the vertical direction (FIGS. 20, 21A and B). In another version, the pressure element is an indenter moving in all the three dimensions (FIGS. 22A and B, 23A–C).

FIGS. 21A and B show the mechanical scanning and measuring unit incorporating a roller in more detail. The base plate 524 is used to produce a controlled pressure on the examined breast. The moving roller 506 acts as the additional dynamic pressure element. The roller 506 is supported by two bearings, 516a and b, which can move vertically along the base plate 524 in the two guide slots, 517a and 517b respectively. The movement of the bearings is controlled by the rotation of the motor 523. The torque of the motor is transferred through gear wheels 521 and 522 to the axis 520. The axis 520 is firmly attached to the pulleys 519b and 519d and through the cables 518a and 518b to the rolling pulleys 519a and 519c, and thus moving the bearings 516a and 516b, and the roller 506, in the vertical direction.

The use of a roller to increase sensitivity of the pressure sensing array to the presence of a tumor in the tissue was discussed for FIGS. 14, and 18A, B, and C.

FIGS. 22A and B show the construction of the mechanical scanning and

In particular, the form of the invention shown in FIGS. 13A, 13B and 13C is especially useful for imaging of breast tissue with tumors situated close to the chest. When a tumor is close to a rib (see FIG. 13A) the approach described above and shown in FIGS. 1–12 as well as ordinary probe techniques, such as palpating or conventional ultrasound, cannot detect the presence of the tumor. However, when the pressure sensing plate 70, having pressure sensor 72 thereon is rolled transversely to the ribs (i.e., the lateral shift) the tumor can be detected easily because of an increased resolution created by rolling the tissue. Indeed, when the tumor is moved near a rib, the rib acts much like the piston/probe 24 shown in FIG. 10 thereby accentuating the peak of the pressure profile corresponding to the location of the tumor or inclusion.

The function P*(x) is shifted laterally reflecting that the peak and baseline of the pressure profile shift. This indicates that there is a harder portion of tissue between the ribs and the surface being pressed upon. If lumps are discovered in this manner, mammography or ultrasound can be utilized for analyzing the internal structures in the region of interest.

In FIG. 14, a device is shown schematically wherein a roller is moved along a section of tissue, and analysis of the differing pressure patterns is made while the roller is being so moved. As shown, a support plate 82 has a number of force sensors 84 thereon in a desired array, and the support plate 82 which also can be backed by a movable force-applying member, is acting against tissue 86. A tumor 87 is located in this tissue.

The lower support is a flexible or semi-rigid sheet 91 against which a roller 92 is pressed through the use of a support carriage 90 mounted on a suitable track 93 for lateral movement in the direction indicated by the double arrows 95. The roller 92 will thus roll along the tissue and cause a raised area 94 of the pad or support 91 to exert a greater deformation of the tissue 86 in a localized area immediately above the roller.

As it rolls along, the tumor 87 will tend to shift from the dotted line position shown at 87, and the stress relationship (as graphed in FIG. 14A) will also shift as the tumor shifts, giving an indication that there is some type of a dislocation in the tissue or different hardness tissue that will shift when the roller is rolled. Again an examination of the stress relationship can be used for determining presence of a tumor, evaluating their hardness and making judgments about its character.

In FIG. 15 a simplified structure for applying deformation to living tissue wherein a quantity of tissue indicated generally at 110 is placed against a support member 112, and a pressure plate 114 is applied to an opposite side of the tissue. Tissue 110 could be breast tissue or could be muscle tissue from a forearm or upper arm, or the like. The edges of the tissue are shown as being defined by boundaries which comprise skin 116. The ends of the tissue could be joined with covering tissue such as skin or joined to other tissue, and could still connected to the human body. The section illustrated is merely intended to be illustrative of the principles involved.

A force-generating device 118 such as a load frame or compression loading frame, which is servo-controlled to provide a known amount of force indicated by the load arrow 120, will be applied to the tissue. The force generator device is capable of being relaxed as desired.

The support plate 112 has an array of individual pressure sensors 122, each of which will provide an individual signal along a line 124 to signal processing equipment 126. The equipment 126 can provide signals to suitable control systems such as in a computer or right back to the operator, so that the operator can adjust the pressure levels to achieve the desired pressure or force across the surface of the support pad 112 which altogether will provide pressure profiles obtained over the surface of the of the tissue and calculate a three-dimensional distribution of internal structures and their relative elasticities. Suitable pressure sensors indicated at 128 also can be carried on the plate 114 in order to increase resolution in detecting deeply situated tumors and evaluating their elasticity, as it was illustrated in FIGS. 11 and 11A.

Thus, FIG. 15 represents a direct force application and a pressure or force readout system that gives the ability to analyze internal structure variations and calculate measuring unit with the movable and extendible indenter 525 which produces a local mechanical stress in the breast. The indenter is attached to two mutually perpendicular cables 543*a* and *b*. The cables pass through the pulleys 528*a* and b, and 529*a* and *b*. The pulleys are mounted at the ends of movable guide bars. The guide bars 526 and 527 are attached respectively to the cables 518*a, b*, and 518*c* and *d*, passing through the pulleys 532*a, b, c*, and *d*, and 533*a, b, c*, and *d*. The cables are pulled by rotating axes 535 and 536, driven by motors 541 and 542 through respective gear wheels 537, 538, and 539, 540.

FIGS. 23A, B, and C show the indenter movement mechanism in more detail. The coordinating element 525*a* which has a disk-shaped base is placed in the slots 530 and 531 respectively of the guide bars 526 and 527 (see FIGS. 22A and 22B). The base of the coordinating element 525*a* is connected to the cables 543*a* and b on the side of the base plate 524 opposite to the breast. The cables 543*a* and 543*b* are connected to the base of the coordinating element 525*a* by the opposite ends. The cable 543*a* passes through the main pulleys 528*a* and *b* and through the auxiliary pulleys 534*a* and *b*. Similarly, the cable 534*b* passes through the main pulleys 529*a* and b and auxiliary pulleys 534*c* and *d*. The base of the indenter is firmly attached to the intersection of the cables 543*a* and 543*b* on the side of the base plate 524 facing the breast in such a way that the indenter always tracks the position of the coordinating element 525*a* defined by the position of the guide bars 526 and 527.

An important feature of this embodiment is that a film pressure sensor 545 is attached to the base of the indenter at the surface facing the base plate. The cables 543*a* and *b* are made of metal strings and serve also as electrical connectors for the pressure sensor. The electrical connection of these cables with the measuring circuit is provided by spring contacts (not shown in figures). The sensor measures the force the indenter applies to the breast. This is similar to having the second pressure sensing array on the side opposite to the array 503. Dependence of the pressure on the position of the indenter over the scanned area of the breast provides a virtual stress pattern over the breast surface facing the indenter. In addition to the 2D motion of the indenter along the surface of the base plate 524, it can also be extended normally to the breast, thus providing a possibility to fully mimic various motions of a palpating finger.

The extension of the indenter is illustrated in FIGS. 23A, B, and C. The indenter is moved by a lead screw 546 and thread bushing 547 pulled by a cable 552. The cable passes through the pulleys 550a and 550b mounted on the movable guide bar 526 and is pulled by a spool fixed on the axis of the motors 552.

Protective housing 544 prevents the examined breast from a direct contact with the moving pulleys and cables.

In the embodiment shown in FIGS. 22–23, motion of the indenter over the breast results in complex temporal and spatial variations of the pressure sensors signals from both sides of the breast. Some of the advantages of obtaining information on the mechanical properties of tissue from both sides of the examined breast were quantitatively analyzed in FIGS. 11, 11A, and 12. The ability of the indenter to "sense" the tissue by extending towards the breast, or making a combined motion in both normal and tangential directions, like an examining human finger does, provides a new dimension in the further processing of the data. In addition, the use of an extendible indenter provides a possibility to create highly localized stress which facilitates the detection of nodules, as it described in FIGS. 10 and 10A.

The motion of the indenter can be controlled either automatically by a computer using a special program designed for optimal scanning, or manually. Manual control can be done in an interactive mode, when an operator observing the stress patterns on the screen of the computer moves the indenter over a region of interest in the breast using a joystick or a mouse. The mouse provides a possibility to control the motion both tangentially, along the breast surface, and normally, towards the breast. The normal motion control button of the mouse can be equipped by a force sensors, so that an operator has a feeling of changes in the local stress caused by the indenter. Consequently, he/she can establish a closer feedback control over the scanning procedure by directly observing the changes in the stress pattern on the screen of the computer resulting from the pressing the normal motion control button with a given force.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. The method of identifying a region within a tissue portion of a human breast having a different elasticity than the surrounding tissue, said method comprising the steps of:

causing a deformation of an examined tissue portion of said breast;

detecting temporal and spatial changes in a pressure pattern caused by said deformation measured on the surface of the examined tissue portion;

defining a model of the tissue portion with homogenous tissue and with boundary conditions corresponding to the examined tissue portion;

evaluation respective temporal and spatial changes in the pressure pattern for said defined model under the same loading conditions as in the detecting step;

adjusting iteratively said defined model by varying a spatial distribution of modulus of elasticity in the model to minimize the difference between said temporal and spatial changes in the pressure pattern obtained in the detecting step and the respective temporal and spatial changes in the pressure pattern evaluated for the adjusted model, thereby obtaining spatial distribution of elasticity modulus in the tissue portion; and visualizing and displaying spatial distribution of modulus of elasticity in said adjusted model of the examined tissue portion for indicating the presence and location of a differing elasticity region of tissue within the examined tissue portion.

2. The method of identifying a region within a tissue portion of a human breast having a different elasticity than the surrounding tissue, said method comprising the steps of:

causing a first deformation of an examined tissue portion of said breast;

causing an additional local second deformation of the surface of the examined tissue portion, the second deformation occurring over a substantially smaller area than the region of the first deformation;

detecting temporal and spatial changes in a pressure pattern caused by said first deformation and said local second deformation measured on the surface of the examined tissue portion;

defining a model of the tissue portion with homogenous tissue and with boundary conditions corresponding to the examined tissue portion;

evaluating respective temporal and spatial changes in the pressure pattern for said defined model under the same loading conditions as in the detecting step; and comparing the temporal and spatial changes in the pressure pattern obtained in the detecting step and the temporal and spatial changes in the pressure pattern evaluated in the evaluating step, the deference indicating the presence and location of a differing elasticity region of tissue within the examined tissue portion.

3. The method of claim 2 including causing said first deformation with a pressure applying means along a line which traverses the surface of the breast.

4. The method of claim 2 including causing said second deformation with extendible indenter which can move in two dimensions across the surface of the breast.

5. The method of claim 4, and further comprising the steps of: scanning said indenter over the breast tissue, measuring pressure exerted by said indenter on the tissue portion as a function of the position of said indenter, thereby obtaining a virtual pattern of stress on the examined tissue surface, detecting and analyzing temporal and spatial changes in said virtual pressure pattern;

evaluating the presence, size and location of regions within a tissue of a human breast having a different elasticity than the surrounding tissue; and displaying evaluated regions of tissue having a different elasticity than the surrounding tissue in an image of the examined tissue portion.

6. The method of claim 5, and further comprising the steps of:

controlling manually the scanning of the indenter over the breast using a mouse which can control the position of the indenter and has a button to control the pressure exerted by the indenter on the tissue; and displaying on the screen of a computer information on the position of the indenter and the exerted pressure, as a feedback information for an operator.

7. A device for identifying a region within an examined tissue portion of a human breast having a different elasticity than the surrounding tissue, said device comprising:

means for causing a first deformation of the examined tissue portion, thereby causing stress and strain in the examined tissue portion;

means for detecting temporal and spatial changes in the pressure pattern measured on the surface of the examined tissue portion;

means for defining a model of the tissue portion with homogeneous tissue and with boundary conditions corresponding to the examined tissue portion;

means for evaluating respective temporal and spatial changes in the pressure pattern for said defined model under the same loading conditions as in the detecting step;

means for comparing the temporal and spatial changes in the pressure pattern obtained in the detecting step and the temporal and spatial changes in the pressure pattern evaluated in the evaluating step, the difference indicating the presence and location of a differing elasticity region of tissue within the tissue portion;

means for adjusting iteratively said defined model by varying a spatial distribution of modulus of elasticity in the model to minimize the difference between said temporal and spatial changes in the pressure pattern obtained in the detecting step and the respective temporal and spatial changes in the pressure pattern evaluated for the adjusting model, thereby and obtaining spatial distribution of elasticity modulus in the tissue portion; and means for visualizing and displaying spatial distribution of modulus of elasticity in said adjusted model of the examined tissue portion to indicate the presence and location of a differing elasticity region of tissue within the examined tissue portion.

8. The device of claim 7 wherein the means for causing a deformation of the tissue portion comprises an additional means producing local first deformation of the surface of the tissue portion, the second deformation occurring over a substantially smaller area than the region of the first deformation.

* * * * *